（12）United States Patent
Wright et al.

(10) Patent No.: US 8,986,306 B2
(45) Date of Patent: Mar. 24, 2015

(54) PATELLA ORTHOPAEDIC SURGICAL METHOD

(75) Inventors: Abraham P. Wright, Warsaw, IN (US);
Kyle B. Thomas, Denver, CO (US); J. Bohannon Mason, Charlotte, NC (US);
Peter F. M. Choong, Fitzroy (AU);
Mark W. Pagnano, Rochester, MN (US); Thomas P. Vail, Durham, NC (US); Raymond E. Randle, Mudaeeraba (AU); James T. Caillouette, Laguna Beach, CA (US); David C. Pollock, Lewisville, NC (US); Jeffrey B Waffensmith, North Oaks, MN (US);
Matthew V Leyden, Saint Paul, MN (US)

(73) Assignee: DePuy (Ireland) (IE)

( * ) Notice: Subject to any disclaimer, the term of this patent is extended or adjusted under 35 U.S.C. 154(b) by 205 days.

(21) Appl. No.: 13/533,607

(22) Filed: Jun. 26, 2012

(65) Prior Publication Data

US 2013/0030539 A1 Jan. 31, 2013

Related U.S. Application Data

(60) Provisional application No. 61/503,159, filed on Jun. 30, 2011.

(51) Int. Cl.
*A61B 17/56* (2006.01)
*A61B 17/15* (2006.01)
*A61B 17/17* (2006.01)
*A61F 2/38* (2006.01)
*A61B 17/00* (2006.01)

(52) U.S. Cl.
CPC ........... *A61B 17/158* (2013.01); *A61B 17/1767* (2013.01); *A61F 2/3877* (2013.01); *A61B 2017/00464* (2013.01)
USPC ............ 606/86 R; 606/88; 606/96; 623/20.18

(58) Field of Classification Search
USPC ......... 606/58, 86 R, 87–88, 96–98, 105, 282; 623/20.15, 20.18–20.2
See application file for complete search history.

(56) References Cited

U.S. PATENT DOCUMENTS

| 2,181,746 | A | 2/1939 | Siebrandt |
| 3,835,849 | A | 9/1974 | McGuire |
| 4,194,861 | A | 3/1980 | Keller |
| D260,927 | S | 9/1981 | Glenn |

(Continued)

FOREIGN PATENT DOCUMENTS

| EP | 0791335 A1 | 8/1997 |
| EP | 0992222 A2 | 4/2000 |

(Continued)

OTHER PUBLICATIONS

Depuy International, Ltd., PFC Sigma Rotating Platform Knee System With MBT Tray, Surgical Technique Brochure, 2003 (43 Pages), Cat. No. 9068-96-000, Depuy International, Ltd., Leeds, England.

(Continued)

*Primary Examiner* — Nicholas Woodall
*Assistant Examiner* — Larry E Waggle, Jr.
(74) *Attorney, Agent, or Firm* — Barnes & Thornburg LLP

(57) ABSTRACT

A method of surgically preparing a patella for implantation of a patella prosthetic component is disclosed.

18 Claims, 21 Drawing Sheets

(56) References Cited

U.S. PATENT DOCUMENTS

| | | | |
|---|---|---|---|
| D281,622 S | 12/1985 | Diamond | |
| 4,565,192 A | 1/1986 | Shapiro et al. | |
| 4,633,862 A | 1/1987 | Petersen | |
| 4,692,073 A | 9/1987 | Martindell | |
| 5,002,547 A | 3/1991 | Poggie et al. | |
| 5,021,055 A * | 6/1991 | Burkinshaw et al. | 606/82 |
| 5,108,401 A | 4/1992 | Insall et al. | |
| 5,116,338 A | 5/1992 | Poggie et al. | |
| 5,129,907 A | 7/1992 | Heldreth et al. | |
| 5,129,908 A | 7/1992 | Petersen et al. | |
| 5,147,365 A | 9/1992 | Whitlock et al. | |
| 5,174,693 A | 12/1992 | Lee et al. | |
| 5,222,955 A | 6/1993 | Mikhail et al. | |
| 5,250,050 A | 10/1993 | Poggie et al. | |
| 5,258,032 A | 11/1993 | Bertin | |
| 5,284,482 A | 2/1994 | Mikhail et al. | |
| 5,284,485 A | 2/1994 | Kammerer et al. | |
| 5,312,409 A | 5/1994 | McLaughlin et al. | |
| 5,382,254 A | 1/1995 | McGarry et al. | |
| 5,415,663 A | 5/1995 | Luckman et al. | |
| 5,470,328 A | 11/1995 | Furnish et al. | |
| 5,484,451 A | 1/1996 | Akopov et al. | |
| D367,531 S | 2/1996 | Price | |
| 5,520,692 A | 5/1996 | Ferrante et al. | |
| 5,536,271 A | 7/1996 | Daly et al. | |
| 5,542,947 A | 8/1996 | Treacy | |
| D373,635 S | 9/1996 | Price | |
| 5,575,793 A | 11/1996 | Carls et al. | |
| 5,582,615 A | 12/1996 | Foshee et al. | |
| 5,593,450 A | 1/1997 | Scott et al. | |
| 5,611,802 A | 3/1997 | Samuelson et al. | |
| 5,626,607 A | 5/1997 | Malecki et al. | |
| 5,667,512 A | 9/1997 | Johnson | |
| 5,716,361 A | 2/1998 | Masini | |
| 5,716,362 A | 2/1998 | Treacy | |
| 5,827,279 A | 10/1998 | Hughett et al. | |
| 5,941,884 A | 8/1999 | Corvelli et al. | |
| 5,944,723 A | 8/1999 | Colleran et al. | |
| 5,957,926 A | 9/1999 | Masini | |
| 5,968,051 A | 10/1999 | Luckman et al. | |
| 6,010,509 A | 1/2000 | Delgado et al. | |
| 6,056,754 A | 5/2000 | Haines et al. | |
| 6,074,425 A | 6/2000 | Pappas | |
| 6,190,391 B1 | 2/2001 | Stubbs | |
| 6,205,884 B1 | 3/2001 | Foley et al. | |
| D459,474 S | 6/2002 | Bratt et al. | |
| 6,419,675 B1 | 7/2002 | Gallo, Sr. | |
| D463,550 S | 9/2002 | Sherman | |
| 6,551,316 B1 | 4/2003 | Rinner et al. | |
| 6,589,248 B1 | 7/2003 | Hughes | |
| 6,851,150 B2 | 2/2005 | Chiang et al. | |
| 6,855,150 B1 | 2/2005 | Linehan | |
| 6,866,667 B2 | 3/2005 | Wood et al. | |
| D549,331 S | 8/2007 | Tomatsu | |
| 7,344,540 B2 | 3/2008 | Smucker et al. | |
| 7,356,902 B2 | 4/2008 | Snider et al. | |
| 7,566,335 B1 | 7/2009 | Scott et al. | |
| 7,632,279 B2 | 12/2009 | Bastian | |
| 7,780,594 B2 | 8/2010 | Hutton | |
| 7,806,899 B2 | 10/2010 | Hogg et al. | |
| 7,878,989 B2 | 2/2011 | McMinn | |
| 7,891,071 B2 | 2/2011 | Collazo | |
| D634,011 S | 3/2011 | Phillips et al. | |
| D638,541 S | 5/2011 | Claypool | |
| 7,972,383 B2 | 7/2011 | Goldstein et al. | |
| D642,678 S | 8/2011 | Dockstader et al. | |
| D646,389 S | 10/2011 | Claypool et al. | |
| 8,216,242 B2 | 7/2012 | Marchyn et al. | |
| 2002/0115987 A1 | 8/2002 | Hildwein et al. | |
| 2003/0163137 A1 | 8/2003 | Smucker et al. | |
| 2004/0153066 A1 | 8/2004 | Coon et al. | |
| 2004/0162561 A1 | 8/2004 | Marchyn et al. | |
| 2005/0240196 A1 | 10/2005 | Davis et al. | |
| 2006/0058886 A1 | 3/2006 | Wozencroft | |
| 2006/0142777 A1 | 6/2006 | Bastian | |
| 2007/0118141 A1 * | 5/2007 | Marchyn et al. | 606/88 |
| 2007/0150066 A1 | 6/2007 | McMinn | |
| 2007/0162031 A1 | 7/2007 | Hogg et al. | |
| 2007/0179626 A1 * | 8/2007 | de la Barrera et al. | 623/20.14 |
| 2007/0233142 A1 | 10/2007 | Oliver | |
| 2007/0260227 A1 | 11/2007 | Phan | |
| 2008/0097450 A1 | 4/2008 | Brown et al. | |
| 2008/0114366 A1 | 5/2008 | Smucker et al. | |
| 2008/0177394 A1 | 7/2008 | Chauhan | |
| 2008/0228190 A1 | 9/2008 | Sherry et al. | |
| 2008/0306484 A1 * | 12/2008 | Coon et al. | 606/88 |
| 2009/0088753 A1 | 4/2009 | Aram et al. | |
| 2009/0264737 A1 | 10/2009 | Haechler et al. | |
| 2009/0326661 A1 | 12/2009 | Wright et al. | |
| 2010/0030223 A1 | 2/2010 | Keller | |
| 2010/0121389 A1 | 5/2010 | Librot et al. | |
| 2010/0152742 A1 | 6/2010 | Nevelös et al. | |
| 2010/0168753 A1 | 7/2010 | Edwards et al. | |
| 2010/0204701 A1 | 8/2010 | Tallarida et al. | |
| 2011/0066193 A1 | 3/2011 | Lang | |
| 2012/0078261 A1 | 3/2012 | Kecman et al. | |
| 2013/0023883 A1 | 1/2013 | Wright et al. | |
| 2013/0023890 A1 | 1/2013 | Kecman et al. | |
| 2013/0030443 A1 | 1/2013 | Wright et al. | |
| 2013/0030539 A1 | 1/2013 | Wright et al. | |
| 2013/0035693 A1 | 2/2013 | Wright et al. | |
| 2013/0079787 A1 | 3/2013 | Spencer Jones et al. | |
| 2013/0079788 A1 | 3/2013 | Spencer Jones et al. | |
| 2013/0079789 A1 | 3/2013 | Randle et al. | |
| 2013/0211410 A1 | 8/2013 | Landes et al. | |

FOREIGN PATENT DOCUMENTS

| | | |
|---|---|---|
| EP | 1723916 | 11/2006 |
| EP | 1967143 A2 | 9/2008 |
| EP | 2574314 | 3/2013 |
| FR | 2737848 A1 | 2/1997 |
| GB | 2433698 | 7/2007 |
| WO | 9945856 A1 | 9/1999 |
| WO | 2005110249 A1 | 11/2005 |
| WO | 2008112996 A1 | 9/2008 |

OTHER PUBLICATIONS

Depuy Orthopaedics, Inc., LCS High Performance Instruments, Surgical Technique Guide, 2008, (44 Pages), Pub. No. 0612-85-506, Depuy Orthopaedics, Inc., Warsaw, IN.

Depuy Orthopaedics, Inc. Sigma High Performance Instruments, Classic Surgical Technique, 2010, (52 Pages), Pub. No. 0612-89-510, Depuy Orthopaedics, Inc., Warsaw, IN.

Depuy Orthopaedics, Inc., Sigma High Performance Instruments, Design Rationale, 2007 (12 Pages), Pub. No. 0612-54-506 (Rev. 2), Depuy Orthopaedics, Inc., Warsaw, IN.

European Search Report, European Pat. App. No. 11175824.9-2310, Dec. 16, 2011 (7 Pages).

European Search Report, European Pat. App. No. 12191753.8-2310, Jan. 3, 2013 (6 Pages).

European Search Report for European Application No. 12174683.8-2310, Sep. 3, 2012, 6 pages.

European Search Report for European Application No. 12174682.0-2310, Sep. 5, 2012, 6 pages.

International Search Report, International Application No. PCT/US12/44947, Oct. 12, 2012, 3 pages.

European Search Report for European Application No. 12186675.0-2310, Dec. 12, 2012, 7 pages.

European Search Report for European Application No. 12186700.6-2310, Dec. 13, 2012, 8 pages.

European Search Report for European Application No. 12186728.7-2310, Dec. 14, 2012, 8 pages.

Declaration of Thomas E. Wogoman (with Exhibits A-I), executed Aug. 11, 2014, 145 pages.

European Search Report for European Application No. 13186416.7-1654 Dec. 6, 2013, 6 pages.

* cited by examiner

PATELLA ORTHOPAEDIC SURGICAL METHOD

This application claims priority under 35 U.S.C. §119 to U.S. Patent Application No. 61/503,159, which was filed on Jun. 30, 2011 and is incorporated herein by reference.

CROSS-REFERENCE

Cross-reference is made to U.S. Provisional Patent Application Ser. No. 61/503,402 entitled "PATELLA RESECTION GUIDE WITH LOCATING FEATURES AND METHOD OF USING THE SAME" by Abraham Wright et al.; U.S. Provisional Patent Application Ser. No. 61/503,404 entitled "PATELLA ORTHOPAEDIC SURGICAL INSTRUMENT ASSEMBLY" by Abraham Wright et al.; U.S. Provisional Patent Application Ser. No. 61/503,164 entitled "PATELLA DRILL GUIDE AND CLAMP ASSEMBLY" by Abraham Wright et al.; co-pending U.S. Design patent application Ser. No. 29/396,508 entitled "MULTIFUNCTIONAL HANDLE" by Abraham Wright et al.; co-pending U.S. Design patent application Ser. No. 29/396,512 entitled "PATELLA RESECTION GUIDE" by Abraham Wright et al.; and co-pending U.S. Design patent application Ser. No. 29/396,514 entitled "COMBINATION PATELLA DRILL GUIDE AND CLAMP" by Abraham Wright et al., each of which is assigned to the same assignee as the present application and each of which is hereby incorporated by reference.

TECHNICAL FIELD

The present disclosure relates generally to orthopaedic surgical instruments and, more particularly, to patella surgical instruments.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella. To secure the prosthetic component to the patella, an orthopaedic surgeon may resect the posterior side of the patient's natural patella to prepare the natural patella to receive the prosthetic component. In use, the patella prosthetic component articulates with the patient's natural or prosthetic femur during extension and flexion of the patient's knee.

To facilitate the replacement of the natural joint with the knee prosthesis, orthopaedic surgeons use a variety of orthopaedic surgical instruments such as, for example, cutting blocks, drill guides, milling guides, and other surgical instruments.

SUMMARY

According to one aspect, an orthopaedic surgical instrument assembly is disclosed. The orthopaedic surgical instrument assembly includes a handle having a housing and a lever moveably coupled to the housing, and a plurality of surgical tools configured to be selectively coupled with the housing. Each surgical tool of the plurality of surgical tools includes a first clamping element and a second clamping element configured to move relative to the first clamping element. The second clamping element is configured to be coupled to the lever such that moving the lever relative to the housing advances the second clamping element toward the first clamping element to clamp a bone of a patient.

In some embodiments, the orthopaedic surgical instrument assembly may include a locking mechanism configured to secure each surgical tool to the housing. The locking mechanism may include a locking bracket that is moveable between a first position in which the locking mechanism secures the surgical tool to the housing and a second position in which the locking mechanism permits the surgical tool to be removed from the housing.

In some embodiments, the housing may have a passageway defined therein. The surgical tool may have a body including the first clamping element and a shaft extending downwardly therefrom. The shaft may be configured to be received in the passageway. The locking bracket may engage the shaft when the locking bracket is placed in the first position and the surgical tool is coupled with the housing. Additionally, in some embodiments, the shaft of the surgical tool may have a notch defined therein. A flange of the locking bracket may be received in the notch when the locking bracket is placed in the first position and may be spaced apart from the notch when the locking bracket is placed in the second position.

In some embodiments, the locking mechanism may further include a biasing member that biases the locking bracket in the first position. In some embodiments, a user-depressible button may be secured to the locking bracket, and the button may be configured such that depressing the button advances the locking bracket from the first position to the second position.

In some embodiments, the housing of the handle may include an upper body having the lever moveably coupled thereto and a grip extending downwardly from the upper body. The lever may include a lever arm extending downwardly from the upper body. The lever arm may be permitted to move relative to the grip when a predetermined amount of force is applied to the lever arm.

Additionally, in some embodiments, the orthopaedic surgical instrument assembly may include a lever release mechanism configured to permit movement of the lever relative to the housing. In some embodiments, the lever release mechanism may include a catch that is moveable between a first position in which the lever is prevented from moving relative to the housing and a second position in which the lever is permitted to move relative to the housing. In some embodiments, the lever release mechanism may further include a plurality of teeth formed on the lever arm. The catch may include a flange that is engaged with the plurality of teeth when the catch is placed in the first position and is spaced from the plurality of teeth when the catch is placed in the second position.

In some embodiments, the lever release mechanism may include a user-depressible button moveably coupled to the upper body. The user-depressible button may have the catch secured thereto such that the catch is placed in the second position when the button is depressed.

In some embodiments, the orthopaedic surgical instrument assembly may further include a biasing member having a first end coupled to the lever arm of the lever and a second end coupled to the housing. The lever may have a first position in which the lever arm is spaced apart from the grip and a second position in which the lever arm is placed in contact with the grip. The biasing member may bias the lever in the first position when the catch is placed in the second position. In some embodiments, the catch may be advanced along the plurality of teeth when the predetermined amount of force is applied to the lever arm.

In some embodiments, the lever may further include an upper lever arm extending outwardly from the upper body, and the second clamping element may include a body having a slot defined therein. The slot may be sized to receive the upper lever arm.

Additionally, in some embodiments, at least one surgical tool of the plurality of surgical tools may be a patella resection guide including a substantially planar upper surface that defines a patella cutting guide surface. The first clamping element may be a stationary first jaw, and the second clamping element may be a second jaw of the patella resection guide that is moveable relative to the stationary first jaw.

In some embodiments, at least one surgical tool of the plurality of surgical tools may be a patella drill guide. The first clamping element may be a stationary first bracket, and the second clamping element may be a second bracket that is moveable relative to the stationary first bracket. The second bracket may have at least one guide hole defined therein sized to receive a surgical drill.

According to another aspect, the orthopaedic surgical instrument assembly includes a handle having a housing, a patella resection guide configured to be selectively coupled with the housing, and a patella drill guide configured to be selectively coupled with the housing. The patella resection guide includes a pair of jaws configured to engage a patient's patella and a substantially planar upper surface that defines a patella cutting guide surface. The patella drill guide includes a first bracket and a second bracket configured to engage a patient's resected patella. The first bracket has at least one guide hole defined therein sized to receive a surgical drill.

In some embodiments, the handle may further include a lever moveably coupled to the housing. The pair of jaws of the patella resection guide may include a first jaw configured to be coupled to the lever such that moving the lever relative to the housing moves the first jaw relative to a second jaw. The first bracket of the patella drill guide may be configured to be coupled to the lever such that moving the lever relative to the housing moves the first bracket relative to the second bracket.

In some embodiments, when the lever is moved in a first direction relative to the housing, the first jaw may move toward the second jaw of the pair of jaws. When the lever is moved in a second direction relative to the housing, the first jaw may move away from the second jaw. Additionally, in some embodiments, when the lever is moved in the first direction relative to the housing, the first bracket may move toward the second bracket, and when the lever is moved in the second direction relative to the housing, the first bracket may move away from the second bracket.

In some embodiments, the lever may include a lever arm. The lever may be permitted to move in the first direction relative to the housing when a predetermined amount of force is applied to the lever arm. In some embodiments, the orthopaedic surgical instrument assembly may further include a lever release mechanism. The lever release mechanism may include a catch that is moveable between a first position in which the lever is prevented from moving relative to the housing unless the predetermined amount of force is applied to the lever arm and a second position in which the lever is permitted to move in the second direction relative to the housing.

According to another aspect, an orthopaedic surgical instrument is disclosed. The orthopaedic surgical instrument includes a housing having an upper body and a grip extending downwardly from the upper body, a locking mechanism configured to selectively secure a plurality of surgical tools to the upper body, and a lever moveably coupled to the upper body. The lever includes a first lever arm extending downwardly from the upper body of the housing. The first lever arm is permitted to move relative to the grip when a predetermined amount of force is applied to the first lever arm. The lever also includes a second lever arm extending outwardly from an upper surface of the upper body. The second lever arm is configured to be coupled to the surgical tool secured to the upper body of the housing.

According to another aspect, the orthopaedic surgical instrument includes a patella resection guide. The patella resection guide includes a body having a substantially planar upper surface that defines a patella cutting guide surface and an inner wall defining an aperture through the body. The aperture is configured to receive a patient's patella and the inner wall includes a first jaw having a first set of teeth extending inwardly into the aperture. The patella resection guide includes a second jaw positioned opposite the first jaw. The second jaw is and movable relative to the first jaw. The second jaw includes a second set of teeth extending inwardly toward the first jaw. The first jaw includes a first tooth of the first set of teeth having a length greater than any other tooth of the first set of teeth, and the second jaw has a second tooth of the second set of teeth that has a length greater than any other tooth of the second set of teeth.

In some embodiments, the second tooth may define a first axis along which the second jaw is movable toward the first jaw. The second jaw may be movable so as to advance into the aperture. In some embodiments, the first tooth may be located along the first axis. Additionally, in some embodiments, the first tooth may be located off-axis relative to the first axis. In some embodiments, the first jaw may include a third tooth extending inwardly into the aperture. The third tooth may be located off-axis relative to the first axis.

In some embodiments, the second tooth and the third tooth may be located approximately equidistant from the first axis. In some embodiments, movement of the second jaw relative to the first jaw may be linear. In some embodiments, the resection guide may further include an arm having the second jaw mounted thereto. The body may have a track defined therein opposite the first jaw, and the arm may be received in the track such that the arm slides along the track to move the second jaw relative to the first jaw.

In some embodiments, the resection guide may further include a saw capture removably coupled to the body, and a cutting slot may be defined between the substantially planar upper surface and the saw capture. In some embodiments, the second tooth may define a first axis along which the second jaw is movable toward the first jaw, and the cutting slot may have a first opening that defines a second axis extending orthogonal to the first axis.

In some embodiments, the body may have a pair of notches defined therein, and the saw capture may include a frame and a pair of lever arms pivotally coupled to the frame. Each lever arm may have a flange and may be moveable between a first position in which the flange is received in a corresponding notch and a second position in which the flange is spaced apart from the corresponding notch such that the saw capture may be removed from the body.

In some embodiments, the orthopaedic surgical instrument may further include a pair of springs that bias the pair of lever arms in the first position. In some embodiments, the resection guide may further have a height gauge including an arm positioned a predetermined distance above the patella cutting guide surface. In some embodiments, the predetermined distance may be approximately 9 millimeters.

According to another aspect, the orthopaedic surgical instrument includes a patella resection guide that has a body including a substantially planar upper surface and a first jaw having a first tooth. The patella resection guide includes a second jaw having a second tooth extending toward the first jaw. The second jaw is moveable relative to the first jaw. The patella resection guide also includes a saw capture removably coupled to the body. A cutting slot is defined between the substantially planar upper surface and the saw capture. The first tooth and the second tooth define an axis of rotation for a patient's patella when the patella is positioned between the first jaw and the second jaw. The cutting slot defines a resection plane that extends through the patient's patella when the patella is positioned between the first jaw and the second jaw.

In some embodiments, the resection guide may further include a height gauge positioned a predetermined distance above the resection plane. In some embodiments, the height gauge may be secured to the saw capture. In some embodiments, the second jaw may be moveable along the axis of rotation defined by the first tooth and the second tooth.

Additionally, in some embodiments, the resection guide may further include a lateral side corresponding to the lateral side of the patient's patella when the patella is positioned between the first jaw and the second jaw and a medial side corresponding to the medial side of the patient's patella when the patella is positioned between the first jaw and the second jaw. The first jaw may be positioned on the lateral side of the resection guide such that the first tooth contacts the lateral side of the patient's patella when the patella is positioned between the first jaw and the second jaw. The second jaw may be positioned on the medial side of the resection guide such that the second tooth is placed in contact with the medial side of the patient's patella when the second jaw is advanced into the opening of the body and the patella is positioned between the first jaw and the second jaw.

In some embodiments, the resection guide may further include a superior side corresponding to the superior side of the patient's patella when the patella is positioned between the first jaw and the second jaw, and an inferior side corresponding to the inferior side of the patient's patella when the patella is positioned between the first jaw and the second jaw. The cutting slot may have a first opening on the superior side of the resection guide. The first opening may be sized to receive a cutting saw blade.

In some embodiments, the first jaw may have a first plurality of teeth. The first tooth may have a length greater than any other tooth of the first plurality of teeth. The second jaw may have a second plurality of teeth. The second tooth may have a length greater than any other tooth of the second plurality of teeth.

According to another aspect, the orthopaedic surgical instrument includes a patella resection guide that has a body having a substantially planar upper surface that defines a patella cutting guide surface and a first jaw having a first plurality of teeth. A first tooth of the first plurality of teeth has a length greater than any other tooth of the first plurality of teeth. The patella resection guide also has a second jaw positioned opposite the first jaw and movable relative to the first jaw. The second jaw includes a second plurality of teeth extending toward the first plurality of teeth. A second tooth of the second plurality of teeth has a length greater than any other tooth of the second plurality of teeth. The second tooth defines an axis along which the second jaw is moveable relative to the first jaw. The patella cutting guide surface may define a resection plane that extends through a patient's patella when the patella is positioned between the first jaw and the second jaw.

According to another aspect, the orthopaedic surgical instrument includes a patella drill guide that has a first bracket and a second bracket coupled to the first bracket that is moveable relative to the first bracket. The second bracket includes a drill plate having a plurality of guide holes defined therein, and each of the plurality of guide holes is sized to receive a surgical drill. A gasket is pivotally coupled to the second bracket, and the gasket has a plurality of plugs configured to be received in the plurality of guide holes of the second bracket.

In some embodiments, the first bracket may include a first side surface that has a first plurality of teeth extending therefrom, and the second bracket may include a second side surface that faces the first side surface such that movement of the second bracket toward the first bracket may cause movement of the second side surface toward to the first side surface. The second side surface may have a second plurality of teeth extending therefrom. In some embodiments, the first side surface of the first bracket may extend substantially parallel to the second side surface of the second bracket.

Additionally, in some embodiments, the gasket may have a first surface facing the second side surface of the second bracket. The first surface may have the plurality of plugs extending therefrom and a plurality of guide holes defined therein configured to receive the second plurality of teeth of the second bracket. In some embodiments, the gasket may have a concave second surface positioned opposite the first surface.

In some embodiments, the second bracket may include an aperture defined in a lower end thereof, and the gasket may include a plug extending from a lower end thereof. The plug may be received in the aperture to pivotally couple the gasket to the second bracket. In some embodiments, the gasket may include a tab extending from an upper end thereof. The tab may include a pair of contoured surfaces configured to receive fingertips of a user such that the user may grip the tab to pivot the gasket relative to the second bracket.

In some embodiments, the gasket may be moveable between a first position in which the gasket is positioned between the drill plate of the second bracket and the first bracket and a second position in which the gasket is spaced apart from the drill plate of the second bracket. In some embodiments, the gasket may be removable from the second bracket. Additionally, in some embodiments, the plurality of guide holes of the drill plate may be arranged in a triangular pattern. In some embodiments, the gasket may be formed from an elastomeric material.

According to another aspect, the orthopaedic surgical instrument includes a handle having a housing and a lever moveably coupled to the housing, and a patella drill guide. The patella drill guide includes a first bracket and a second bracket that is moveable relative to the first bracket. The second bracket is coupled to the lever such that moving the lever relative to the housing moves the second bracket relative to the first bracket. A gasket is pivotally coupled to at least one of the first bracket and the second bracket. The first bracket and the second bracket are configured to engage a patient's resected patella. The patella drill guide also includes a guide hole that is sized to receive a surgical drill and is defined in at least one of the first bracket and the second bracket. The gasket has a plug that is configured to be received in the guide hole.

In some embodiments, the second bracket may include a drill plate having the guide hole defined therein. In some embodiments, the gasket may be moveable between a first position in which the gasket is positioned between the drill plate of the second bracket and the first bracket and a second position in which the gasket is spaced apart from the drill plate of the second bracket.

In some embodiments, when the lever is moved in a first direction relative to the housing, the second bracket may be moved toward the first bracket, and when the lever is moved in a second direction relative to the housing, the second bracket may be moved away from the first bracket.

According to another aspect, the orthopaedic surgical instrument includes a patella drill guide. The patella drill guide includes a first bracket and a second bracket coupled to the first bracket and moveable relative to the first bracket. The second bracket includes a drill plate having a plurality of teeth extending therefrom and a first plurality of guide holes defined therein. Each of the first plurality of guide holes is sized to receive a surgical drill. A gasket is pivotally coupled to the second bracket, and the gasket has a second plurality of guide holes defined therein configured to receive the plurality of teeth of the second bracket and a plurality of plugs configured to be received in the first plurality of guide holes of the second bracket. The gasket is moveable between a first position in which the gasket is positioned between the drill plate of the second bracket and the first bracket, and a second position in which the gasket is spaced apart from the drill plate of the second bracket.

According to another aspect, a method of surgically preparing a patella for implantation of a patella prosthetic component is disclosed. The method includes positioning the patella between a pair of jaws of a patella resection guide, rotating the patella about a first axis extending in an inferior-superior direction to adjust the medial-lateral tilt of the patella, engaging the pair of jaws with the patella such that rotation about the first axis is prevented, rotating the patella about a second axis extending in a medial-lateral direction to adjust the inferior-superior tilt of the patella, clamping the pair of jaws to the patella such that rotation about the first axis and the second axis is prevented, and engaging the patella with a cutting saw blade. In some embodiments, the pair of jaws may include a stationary first jaw and a second jaw that is moveable relative to the first jaw.

In some embodiments, engaging the pair of jaws may further include engaging a first spike of the first jaw with the lateral side of the patella and advancing a second spike of the second jaw into contact with the medial side of the patella. In some embodiments, the first tooth and the second tooth may define the second axis, and rotating the patella about the second axis may include rotating the patella on the first tooth and the second tooth.

In some embodiments, clamping the pair of jaws with the patella may include engaging additional teeth of the first jaw with the lateral side of the patella and engaging additional teeth of the second jaw with the medial side of the patella. In some embodiments, positioning the patella between the pair of jaws may include contacting the patella with a height gauge of the patella resection guide.

In some embodiments, the method may further include securing a saw capture to a body of the resection guide. The body may have the pair of jaws coupled thereto. Additionally, in some embodiments, the method may further include measuring the patella to determine a level of bone resection. Engaging the patella with the cutting saw blade may include cutting the patella to the level of bone resection.

According to another aspect, the method of surgically preparing a patella for implantation of a patella prosthetic component includes attaching a patella resection guide to a handle, operating a lever of the handle to engage a pair of jaws of the patella resection guide with a patient's patella, engaging the patella with a cutting saw blade to resect the patella and create a resected patella, detaching the patella resection guide from the handle, attaching a patella drill guide to the handle, operating the lever of the handle to clamp the resected patella between a pair of brackets of the patella drill guide, and drilling at least one mounting hole in the resected patella.

In some embodiments, operating the lever of the handle to engage the pair of jaws may include contacting the lateral side of the patella with a first jaw and applying an amount of force to the lever to advance a second jaw into contact with the medial side of the patella. In some embodiments, operating the lever of the handle to engage the pair of jaws may include engaging a first tooth of the first jaw with the lateral side of the patella and engaging a second tooth of the second jaw with the medial side of the patella.

In some embodiments, the method may further include rotating the patella about a first axis extending in an inferior-superior direction to adjust the medial-lateral tilt of the patella and operating the lever of the handle to clamp the pair of jaws to the patella such that additional rotation about the first axis is prevented prior to engaging the patella with the cutting saw blade.

In some embodiments, detaching the patella resection guide may include operating the lever to withdraw the second jaw from the medial side of the resected patella. In some embodiments, operating the lever of the handle to clamp the patella between the pair of brackets may include contacting the anterior side of the resected patella with a first bracket and advancing a second bracket into contact with the posterior side of the resected patella. Additionally, in some embodiments, drilling at least one mounting hole in the resected patella may include advancing a surgical drill through one of a plurality of guide holes defined in the second bracket.

In some embodiments, the method may include operating the lever to withdraw the second bracket from the posterior side of the resected patella after drilling at least one mounting hole, attaching a patella prosthetic component on the posterior side of the resected patella, and operating the lever to clamp the patella prosthetic component and the resected patella between the pair of brackets.

In some embodiments, the method may further include positioning a gasket between the patella prosthetic component and the second bracket prior to operating the lever to clamp the patella prosthetic component and the resected patella between the pair of brackets.

According to another aspect, the method of surgically preparing a patella for implantation of a patella prosthetic component includes positioning a resected patella between a first bracket and a second bracket of a patella drill guide, engaging the first bracket and the second bracket with the resected patella, advancing a surgical drill through one of a plurality of guide holes defined in the second bracket, drilling at least one mounting hole in the resected patella, disengaging the second bracket from the resected patella, attaching the patella prosthetic component to the resected patella, rotating a gasket coupled to the second bracket into position between the second bracket and the patella prosthetic component, and clamping the gasket, the patella prosthetic component, and the resected patella between the first bracket and the second bracket.

In some embodiments, engaging the first bracket and the second bracket with the resected patella may include engaging a first plurality of teeth formed on the first bracket with anterior side of the resected patella and engaging a second plurality of teeth formed on the second bracket with the posterior side of the resected patella. In some embodiments, rotating the gasket coupled to the second bracket may include placing each plug of a plurality of plugs extending from the gasket into each guide hole of the plurality of guide holes of the second bracket.

BRIEF DESCRIPTION OF THE DRAWINGS

The detailed description particularly refers to the following figures, in which.

DETAILED DESCRIPTION OF THE DRAWINGS

Figure 1:
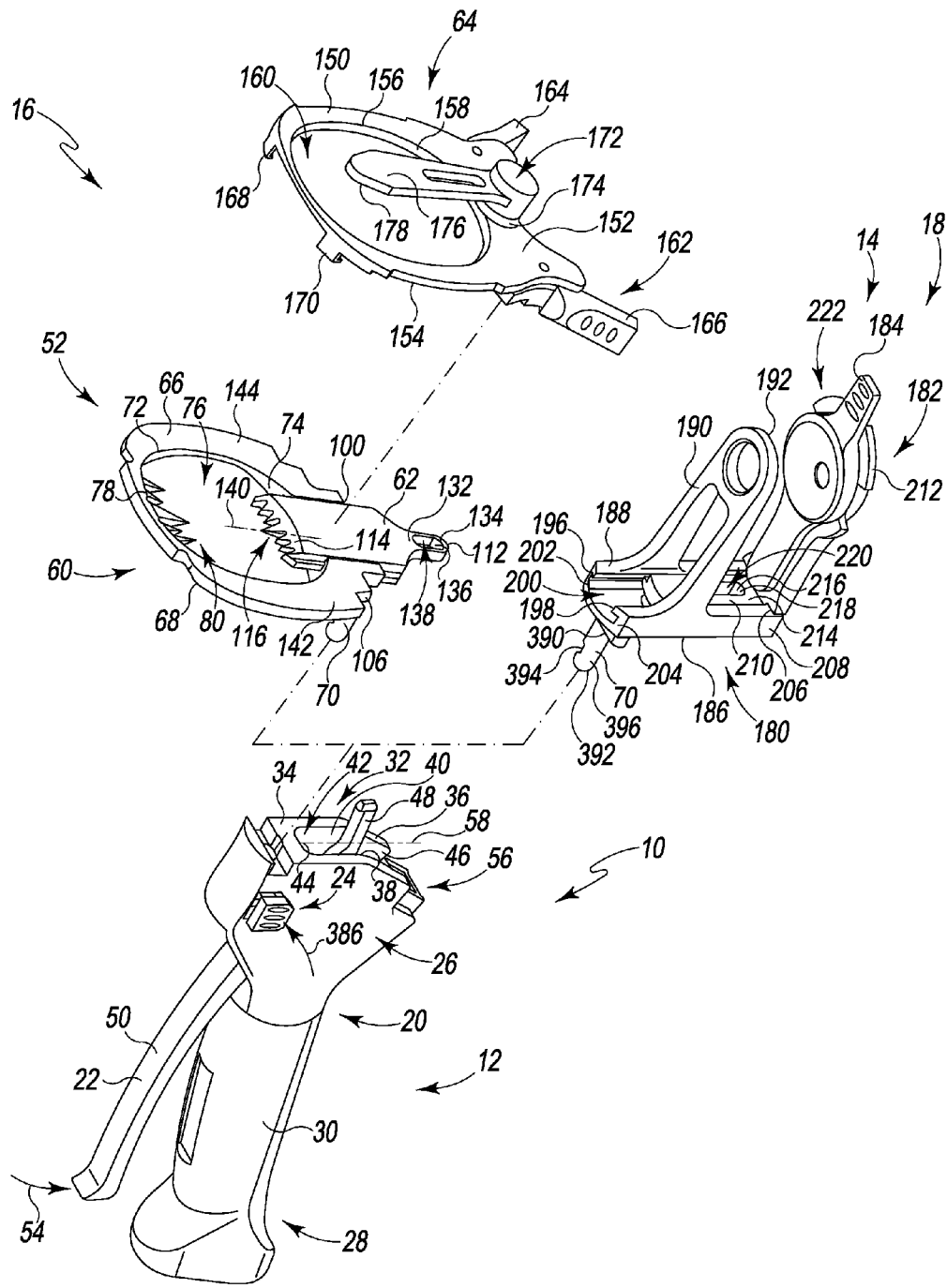
FIG. 1 is an exploded, perspective view of an orthopaedic surgical instrument assembly.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, an orthopaedic surgical instrument assembly 10 (hereinafter assembly 10) includes a multifunctional handle 12 and a plurality of orthopaedic surgical instruments or tools 14. In the illustrative embodiment, the surgical tools 14 to be selectively coupled with the handle 12 include a patella resection guide 16 and a patella drill guide 18. However, in other embodiments, additional and/or other surgical tools 14 may be used with the multifunctional handle 12.

As described in greater detail below, the orthopaedic surgical instrument assembly 10 is utilized to surgically prepare a patient's patella for implantation of a patella prosthetic component, such as a patella prosthetic component 610 (see FIG. 5). The patient's patella may be positioned in the patella resection guide 16 and may be resected by use of, for example, a surgical saw. Thereafter, the resected patella may be positioned in the patella drill guide 18, and the surgeon may use the drill guide 18 to drill guide holes into the resected patella. The surgeon may use the drill guide 18 to size and select a patella prosthetic component. After the patella prosthetic component is selected, the surgeon may use the drill guide 18 to secure patella prosthetic component to the resected patella.

The multifunctional handle 12 includes a housing 20, a lever 22 moveably coupled to the housing 20, and a locking mechanism 24 configured to secure each surgical tool 14 to the housing 20. The housing 20 has an upper body 26, a lower body 28 extending downwardly therefrom, and a grip 30 attached to the lower body 28 that is sized to receive the hand of a user. The upper body 26 of the handle 12 has a mounting surface 32 that supports a surgical tool 14 when the surgical tool 14 is coupled to the handle 12.

The mounting surface 32 of the handle 12 includes a substantially planar section 34 and an inclined section 36 extending downwardly at an angle relative to the section 34. An opening 38 is defined in the mounting surface 32, and the upper body 26 of the housing 20 includes an inner wall 40 extending downwardly from the opening 38. The inner wall 40 defines a channel 42 having a closed end 44 and an open end 46. The closed end 44 of the channel 42 is positioned in the substantially planar section 34 of the mounting surface 32 and the open end 46 of the channel 42 is defined in the inclined section 36.

The lever 22 of the multifunctional handle 12 is pivotally coupled to the upper body 26 of the housing 20. The lever 22 has an upper lever arm 48 that is received in the channel 42. As shown in FIG. 1, the lever arm 48 extends outwardly through the opening 38 of the mounting surface 32. The lever 22 also has a bowed trigger arm 50 that extends downwardly from the upper body 26 of the handle 12.

In use, the handle 12 is operable to control the operation of the surgical tools 14. For example, when a predetermined amount of force is applied to the trigger arm 50 in the direction indicated by arrow 54, the upper lever arm 48 is advanced linearly toward the closed end 44 of the channel 42 along a longitudinal axis 58. The handle 12 also includes a lever release mechanism 56 configured to permit the upper lever arm 48 to move in either direction along the axis 58, as will be described in greater detail below.

Turning to the surgical tools 14 shown in FIG. 1, the patella resection guide 16 includes a patella clamp 52 and a saw capture 64 configured to be removably coupled to the clamp 52. The clamp 52 includes a body 60 and a clamping arm or slide arm 62 moveably coupled to the body 60. The body 60 of the clamp 52 is formed from an implant grade metallic material such as steel, titanium, or cobalt chromium. It will be appreciated that in other embodiments the body 60 may be formed from a polymeric material such as polyethylene or ultra-high molecular weight polypropylene (UHMWPE). The body 60 has a substantially planar upper surface 66 and a lower surface 68 positioned opposite the upper surface 66. A mounting bracket 70, which is configured to be secured to the handle 12 via the locking mechanism 24, extends downwardly from the lower surface 68 of the clamp 52. When the clamp 52 is secured to the handle 12, a portion of the lower surface 68 of the clamp 52 is supported by the mounting surface 32 of the handle 12.

The upper surface 66 of the clamp 52 has an opening 72 defined therein. The body 60 includes a curvilinear inner wall 74 that extends downwardly from the upper surface 66 to the lower surface 68, thereby defining a substantially elliptical or oval-shaped aperture 76 through the body 60. The aperture 76 is sized to receive a patient's patella, as will be described in greater detail below. It will be appreciated that in other embodiments the aperture 76 may have a different size or shape, such as, for example, a square, rectangle, or other shape properly sized to receive a patient's patella.

Figure 3A:
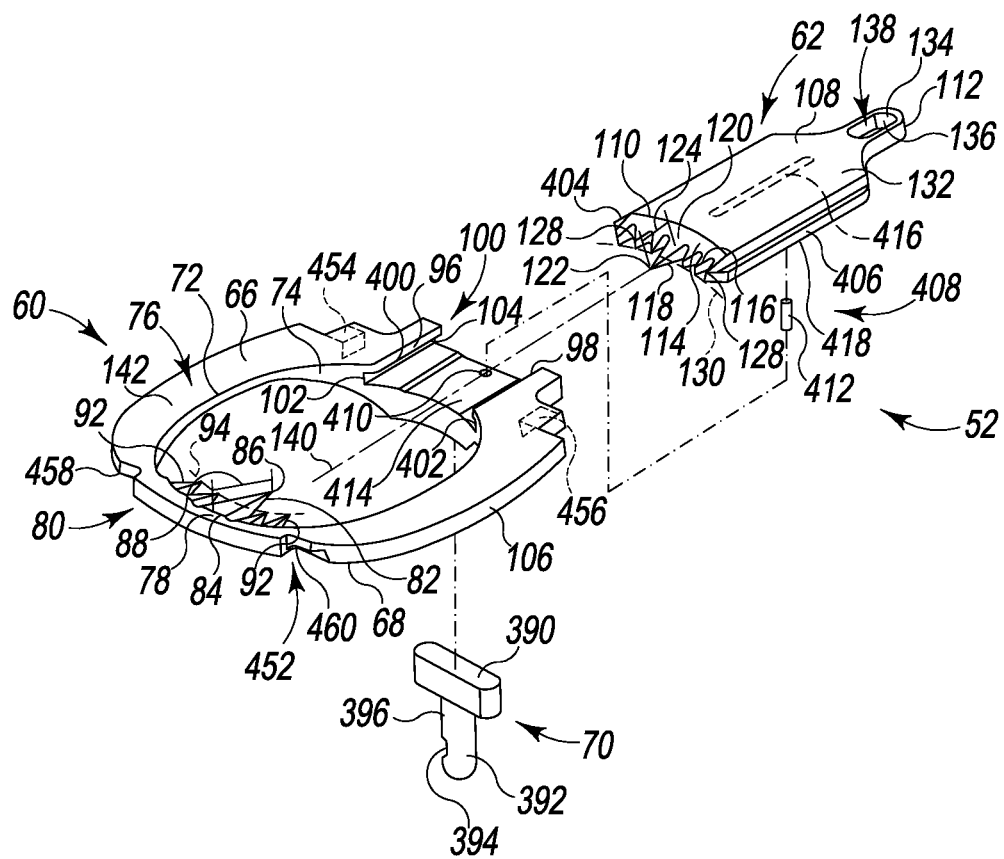
FIG. 3A is an exploded, perspective view of a patella clamp of the patella resection guide of the orthopaedic surgical instrument assembly of FIG. 1.

As best seen in FIG. 3A, the body 60 of the patella clamp 52 also includes a jaw 78 extending from the inner wall 74. The jaw 78 is embodied as a plurality of teeth 80 that extend inwardly into the aperture 76. The teeth 80 include an elongated tooth 82. When the elongated tooth 82 is measured from a base 84 at the inner wall 74 to a tip 86 spaced apart from the inner wall 74, the elongated tooth 82 has a length 88 greater than any of the other teeth 80. The tips 92 of the remaining teeth 80 define an arc 94 within the aperture 76. The tip 86 of the tooth 82 extends beyond the arc 94 into the aperture 76.

The body 60 of the clamp 52 further includes a pair of inner sidewalls 96, 98 that extend downwardly from the upper surface 66 to define a track 100 in the body 60. The track 100 includes an opening 102 defined in the inner wall 74 opposite the jaw 78. The track 100 includes another opening 104 defined in the outer wall 106 of the body 60. As shown in FIG. 3A, the opening 104 is positioned opposite the opening 102.

The slide arm 62 of the clamp 52 is positioned in the track 100 and, as will be described in greater detail below, is configured to slide along the track 100. The slide arm 62 is formed from an implant grade metallic material such as steel, titanium, or cobalt chromium. It should be appreciated that in other embodiments the slide arm 62 may be formed from a polymeric material such as polyethylene or UHMWPE. The slide arm 62 has a main body 108 including an end 110 positioned opposite the jaw 78 of the body 60 and another end 112 configured to engage the lever 22 of the multifunctional handle 12. The slide arm 62 also includes a moveable jaw 114 formed at the end 110.

As shown in FIG. 3A, the moveable jaw 114 is positioned opposite the jaw 78. The jaw 114, like the jaw 78, is embodied as a plurality of teeth 116 that extend toward the jaw 78. The teeth 116 include an elongated tooth 118. The elongated tooth 118 has a length 124, which is measured from a base 120 to a tip 122, that is greater than any of the other teeth 116. The tips 128 of the remaining teeth define an arc 130 in the aperture 76. The tip 122 of the tooth 118 extends beyond the arc 130.

Returning to FIG. 1, the body 108 of the slide arm 62 of the clamp 52 has an upper surface 132 that is substantially flush with the planar upper surface 66 of the body 60 of the clamp 52. The upper surface 132 of the slide arm 62 has an opening 134 defined at the end 112 of the slide arm 62, and the slide arm 62 includes an inner wall 136 that extends downwardly from the opening 134. The inner wall 136 defines a slot 138 through the slide arm 62 that is sized to receive the upper lever arm 48 of the multifunctional handle 12.

Figure 7:
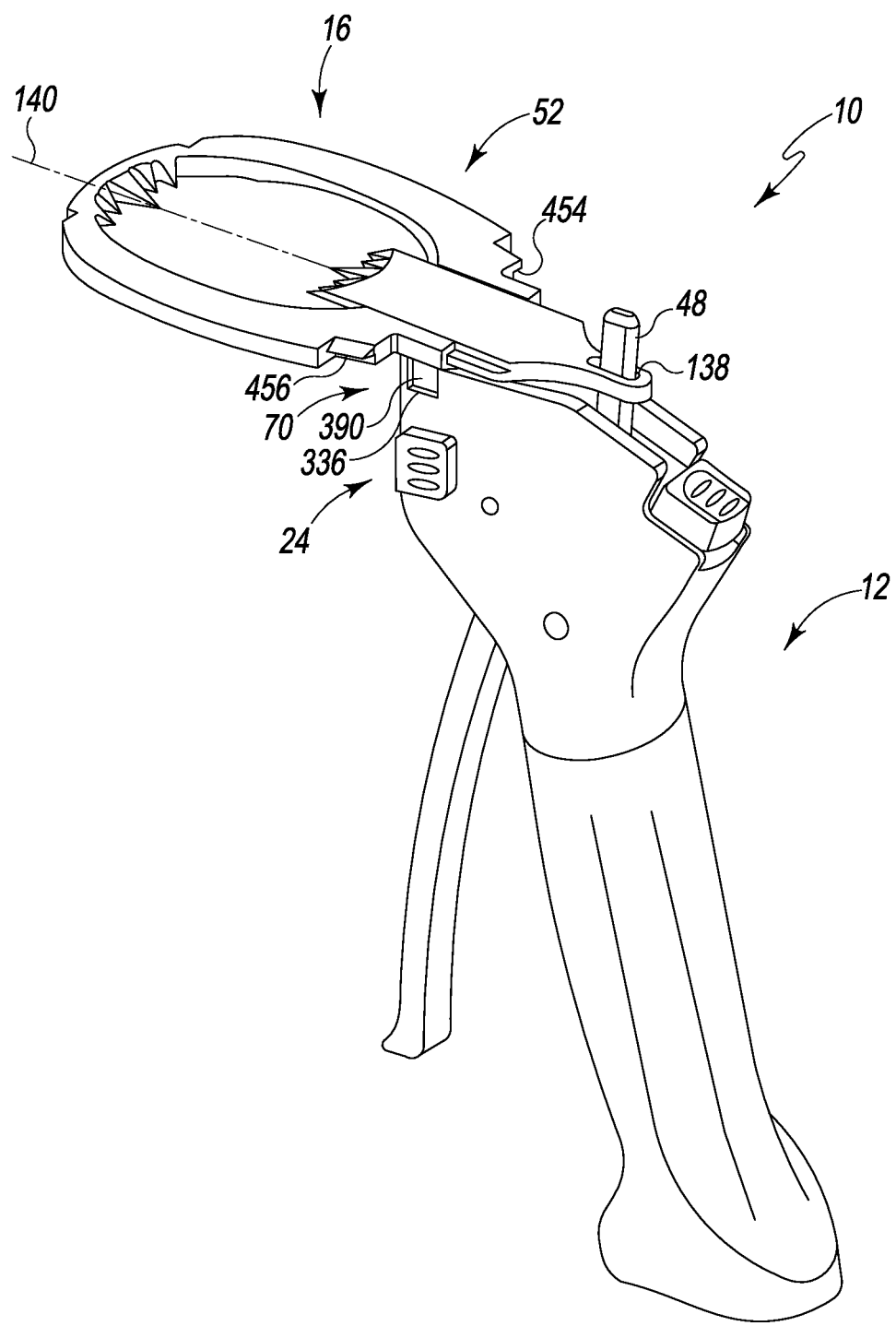
FIG. 7 is a perspective view of the orthopaedic surgical instrument assembly of FIG. 1 showing the patella clamp of the patella resection guide attached to the multifunctional handle.

In use, when the patella resection guide 16 is coupled to the handle 12 as shown in FIG. 7, the lever arm 48 is configured to act on the inner wall 136 of the clamp 52 to move the jaw 114 relative to the stationary jaw 78. As the upper lever arm 48 moves linearly along the axis 58 relative to the housing 20, the lever arm 48 acts on the inner wall 136 of the clamp 52 to advance the slide arm 62 along the track 100, thereby moving the jaw 114 relative to the jaw 78. The slide arm 62 moves linearly along an axis 140 that is defined by the tooth 118 of the moveable jaw 114. When the resection guide 16 is coupled to the handle 12, the axis 140 is substantially aligned with the axis 58.

As will be described in greater detail below in reference to FIGS. 9-13, the teeth 80, 116 of the jaws 78, 114 are configured to engage a patient's patella during a surgical procedure to hold the patella in position during a resection procedure. The clamp 52 also includes a planar upper surface 66, which is usable by the orthopaedic surgeon to guide the surgical saw blade during the resection procedure, as will be described in greater detail below. In that way, the planar upper surface 66 is an open cutting guide surface 144. The cutting guide surface 144 defines a resection plane 142 that extends through the patella when the patella is positioned between the jaws 78, 114 in the aperture 76.

As described above, the resection guide 16 also includes the saw capture 64, which is configured to be removably coupled to the clamp 52 to form a closed cutting guide. It should be appreciated that in other embodiments the resection guide 16 may not include the saw capture 64. The saw capture 64 includes a frame 150 formed from an implant grade metallic material such as steel, titanium, or cobalt chromium. It should be appreciated that in other embodiments the frame 150 may be formed from a polymeric material such as polyethylene or UHMWPE.

As shown in FIG. 1, the frame 150 of the saw capture 64 has an upper surface 152 and a substantially planar lower surface 154 positioned opposite the upper surface 152. The upper surface 152 of the frame 150 has an opening 156 defined therein. The frame 150 includes a curvilinear inner wall 158 that extends downwardly from the upper surface 152, and the inner wall 158 defines an oval-shaped aperture 160 through the frame 150. The aperture 160, like the aperture 76, is sized to receive a patient's patella. As shown in FIG. 1, the shape and size of the aperture 160 substantially matches the shape of the aperture 76 defined in the clamp 52 such that the apertures 76, 160 are in registry with each other when the saw capture 64 is coupled to the clamp 52. It will be appreciated that in other embodiments the aperture 160, like the aperture 76, may take any other shape sized to receive a patient's patella.

The saw capture 64 of the resection guide 16 also includes an attachment mechanism 162 configured to secure the saw capture 64 to the clamp 52. In the illustrative embodiment, the attachment mechanism 162 includes a pair of mounting arms 164, 166 pivotally coupled to the frame 150 and a pair of mounting brackets 168, 170 extending downwardly from the lower surface 154 of the frame 150. As will be described in greater detail below, the arms 164, 166 and brackets 168, 170 engage predefined areas of the body 60 of the clamp 52 to secure the saw capture 64 thereto, and the arms 164, 166 pivot relative to the frame 150 to permit the saw capture 64 to be attached or detached from the clamp 52.

As shown in FIG. 1, the patella resection guide 16 also includes a height gauge 172 secured to the saw capture 64. In other embodiments, the height gauge 172 may be directly secured to the clamp 52 rather than the saw capture 64. The height gauge 172 has a base 174 formed on the upper surface 152 of the frame 150 and a stylus arm 176 pivotally coupled to the base 174. The stylus arm 176 has a lower surface 178 that is configured to be located at a predetermined height above the planar upper surface 66 of the body 60.

As described above, the surgical tools 14 also includes the patella drill guide 18. As shown in FIG. 1, the patella drill guide 18 includes a support bracket 180, a clamping bracket or drill bracket 182 movably coupled to the support bracket 180, and a compression gasket 184 pivotally coupled to the drill bracket 182. The support bracket 180 and the drill bracket 182 are formed from an implant grade metallic material such as steel, titanium, or cobalt chromium. It will be appreciated that in other embodiments the support bracket 180 and/or the drill bracket 182 may be formed from a polymeric material such as polyethylene or UHMWPE.

The support bracket 180 of the drill guide 18 includes a lower surface 186 that is supported by the mounting surface 32 of the handle 12 when the drill guide 18 is secured thereto. Like the resection guide 16, the drill guide 18 includes a mounting bracket 70 that extends downwardly from the lower surface 186, and the mounting bracket 70 is configured to be secured to the handle 12 via the locking mechanism 24.

The support bracket 180 of the drill guide 18 also includes an upper surface 188 positioned opposite the lower surface 186. The support bracket 180 also has a stationary arm 190 extending upwardly from the upper surface 188. The stationary arm 190 includes a backing plate 192 configured to receive the anterior surface of a patient's patella, as will be described in greater detail below.

The support bracket 180 also includes a pair of side walls 196, 198 that extend downwardly from the upper surface 188 to define a track 200 in the support bracket 180. The track 200 includes an opening 202 defined in an end 204 of the support bracket 180 and another opening 206 defined in an opposite end 208. As shown in FIG. 1, the drill bracket 182 is positioned in the track 200 and, as will be described in greater detail below, is configured to slide along the track 200.

As shown in FIG. 1, the drill bracket 182 of the drill guide 18 has a slide frame 210 that is positioned in the track 200. The drill bracket 182 also includes a moveable arm 212 extending upwardly from an upper surface 214 of the slide frame 210. As shown in FIG. 1, the arm 212 is positioned parallel to the arm 190 of the support bracket 180. The moveable arm 212 includes a drill plate 222 that is used to guide the drilling operations performed on the resected patella, as will be described in greater detail below.

The upper surface 214 of the slide frame 210 has an opening 216 defined therein. The slide frame 210 includes an inner wall 218 that extends downwardly from the opening 216 to define a slot 220 through the slide frame 210. The slot 220 is sized to receive the upper lever arm 48 of the handle 12 when the drill guide 18 is coupled thereto. In that way, as the upper lever arm 48 of the handle 12 moves within the channel 42 of the handle 12, the lever arm 48 acts on the slide frame 210 to slide the drill bracket 182 linearly along the track 200 and move the bracket 182 relative to the bracket 180.

Figure 2:
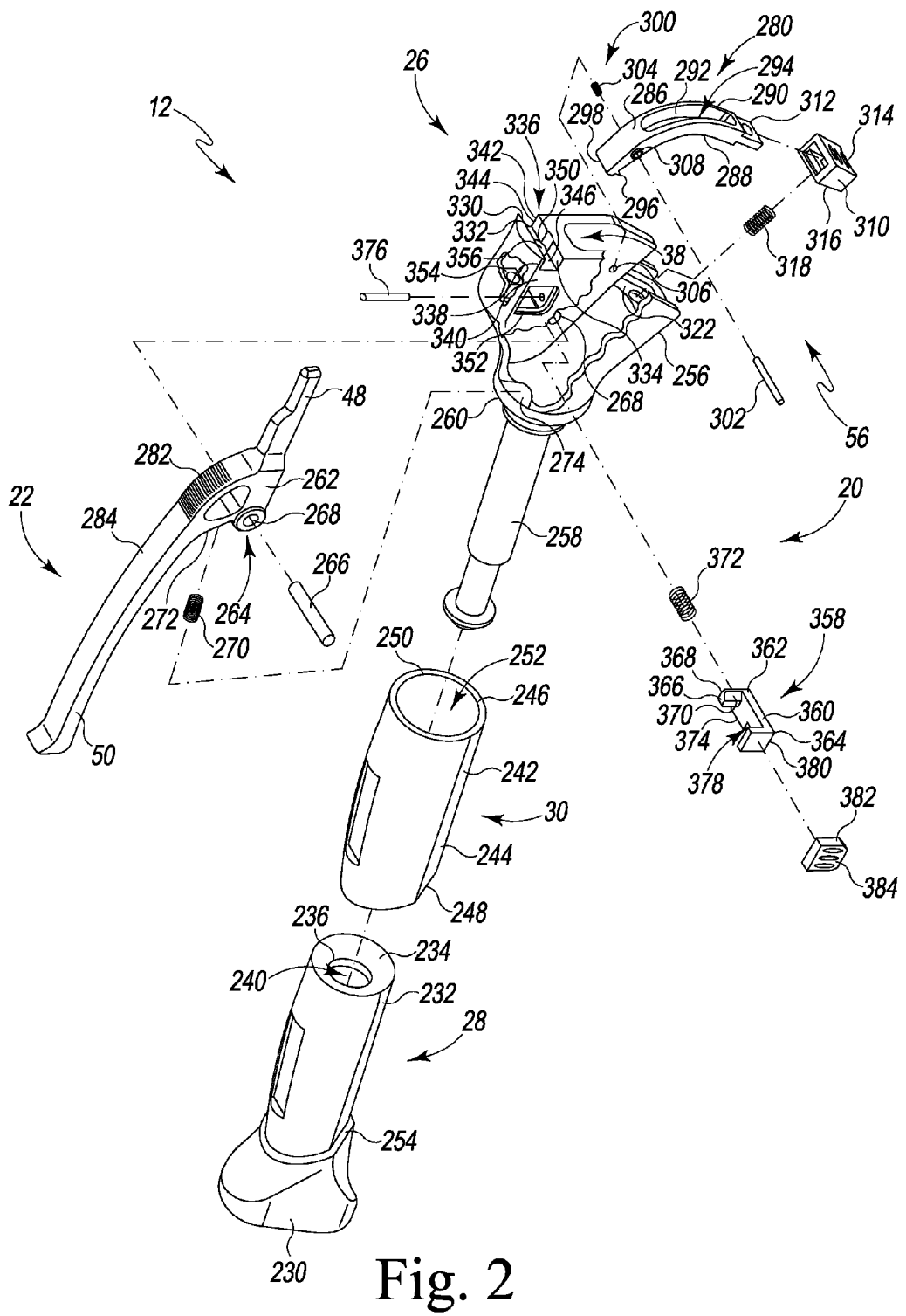
FIG. 2 is an exploded, perspective, partial cross-sectional view of a multifunctional handle of the orthopaedic surgical instrument assembly of FIG. 1.
Figure 3B:
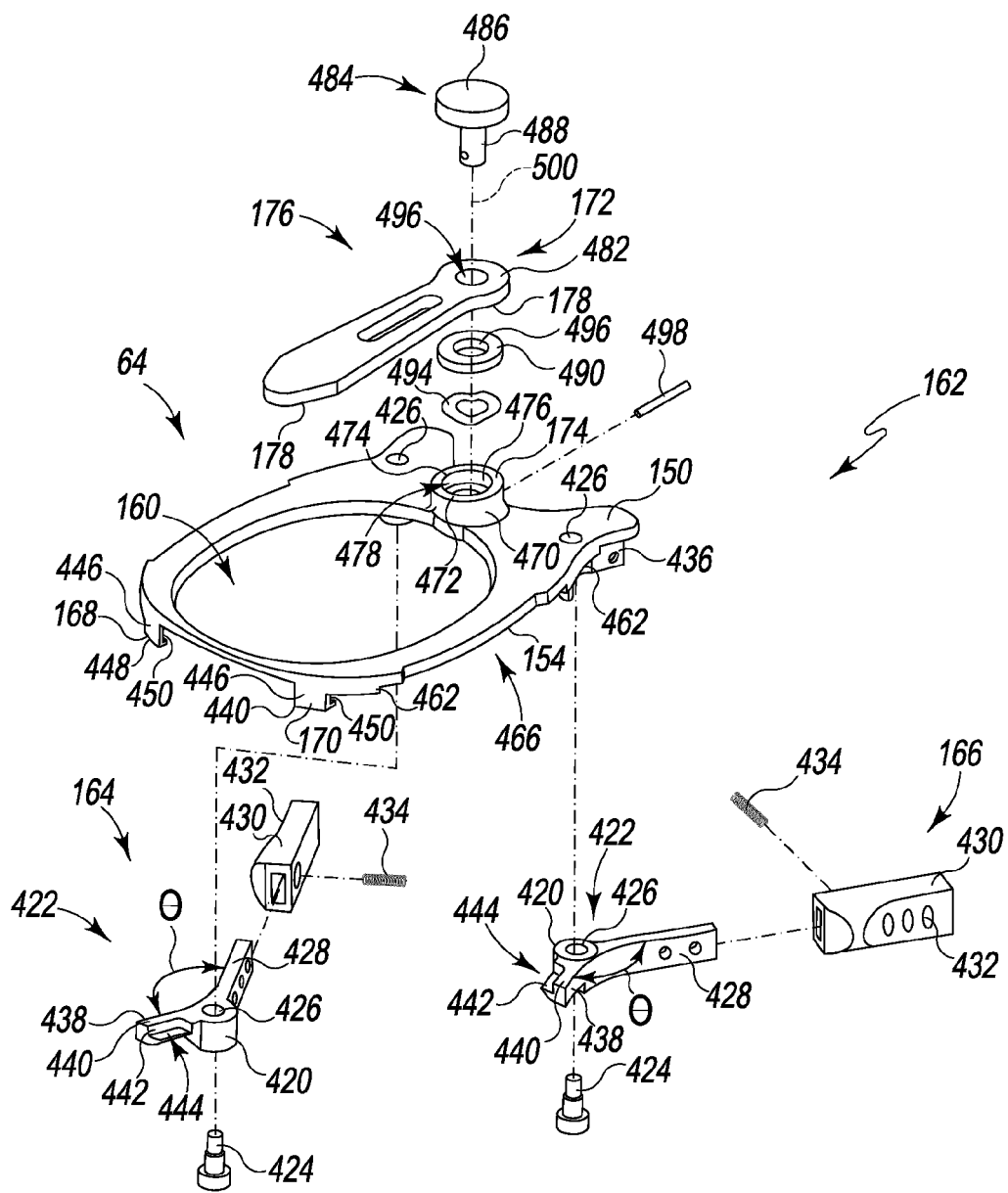
FIG. 3B is an exploded, perspective view of a saw capture of the patella resection guide of the orthopaedic surgical instrument assembly of FIG. 1.
Figure 4:
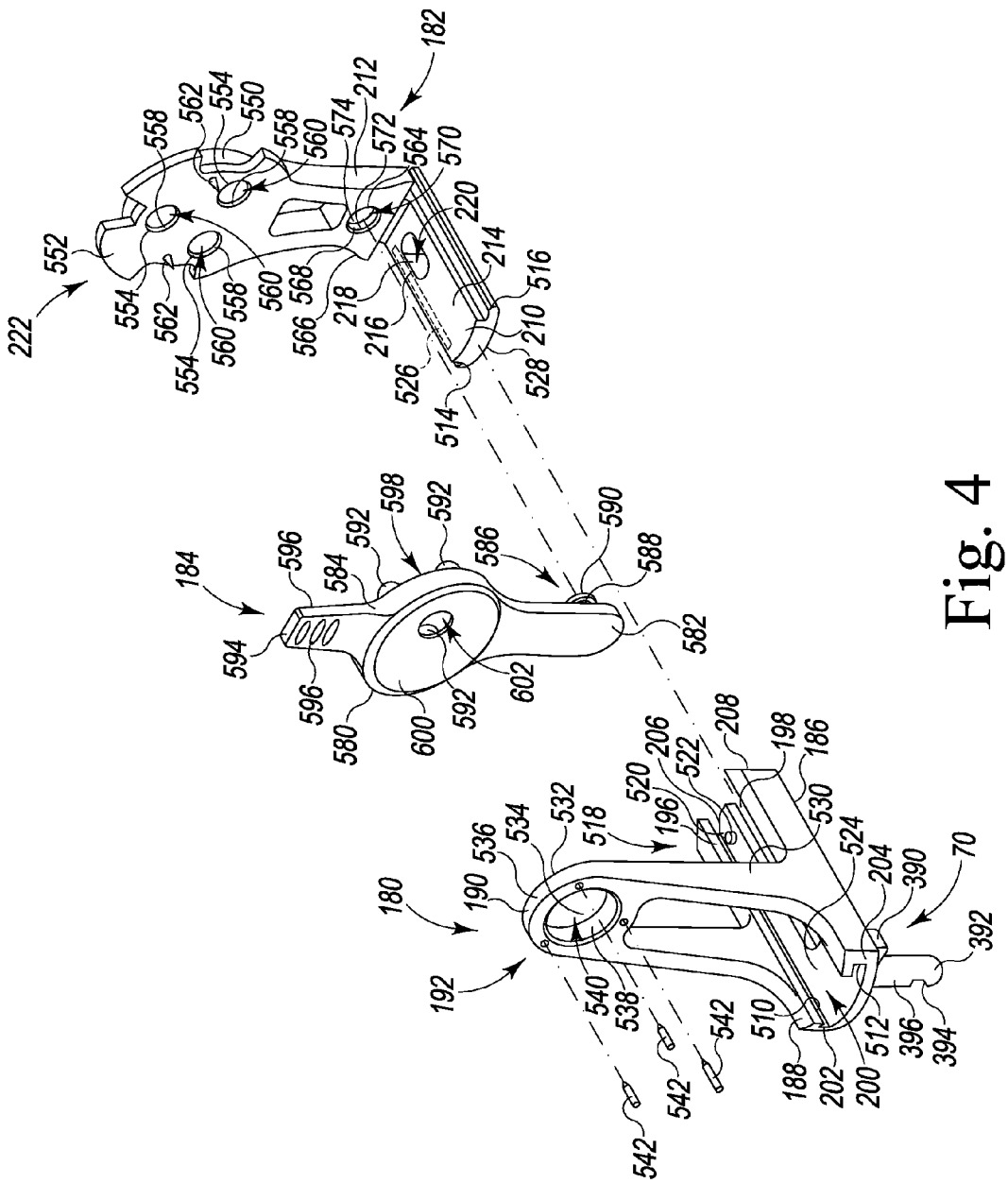
FIG. 4 is an exploded, perspective view of a patella drill guide of the orthopaedic surgical instrument assembly of FIG. 1.

Referring now to FIGS. 2-4, the multifunctional handle 12, the resection guide 16, and the drill guide 18 are shown in greater detail. Referring in particular to FIG. 2, the handle 12 is shown partially dissembled. As described above, the handle 12 includes the housing 20, which has the upper body 26 that is attached to the lower body 28. The lower body 28 has a base 230 and a casing 232 extending upwardly from the base 230 to an upper end 234. A circular opening 236 is defined in the upper surface 238 of the casing 232, and the lower body 28 includes a hollow passageway 240 that extends downwardly from the opening 236 into the casing 232.

The grip 30 of the multifunctional handle 12 is positioned over the casing 232 of the lower body 28. The grip 30 has a shell 242 that includes an outer surface 244 extending from a top end 246 to a bottom end 248, and the shell 242 has an opening 250 defined in the top end 246 thereof. A cylindrical passageway 252 extends downwardly from the opening 236 through the shell 242. In the illustrative embodiment, the grip 30 is molded over the lower body 28 such that the passageway 252 is formed around the casing 232. It should be appreciated that in other embodiments the passageway 252 of the grip 30 may be sized such that the shell 242 slides over the casing 232 to assemble the grip 30 with the lower body 28. The bottom end 248 of the grip 30 contacts the upper edge 254 of the base 230 and the top end 246 of the grip 30 is substantially flush with the upper end 234 of the lower body 28.

The casing 232 of the lower body 28 is formed from silicone. It will be appreciated that in other embodiments the casing 232 may be formed from a polymeric material such as polyethylene or ultra-high molecular weight polypropylene (UHMWPE) or an implant grade metallic material such as steel, titanium, or cobalt chromium. The grip 30 and the base 230 are formed from a stiff elastomeric material, but in other embodiments may be formed from a suitable polymeric material.

As shown in FIG. 2, the multifunctional handle 12 also includes the upper body 26, which includes an outer casing 256 and a shaft 258 extending downwardly therefrom. When the upper body 26 is attached to the lower body 28, the shaft 258 is received in the passageway 240 of the lower body 28, and a lower edge 260 of the upper body 26 contacts the lower body 28 and the grip 30. As shown in FIG. 2, the lever 22 and the lever release mechanism 56 are coupled to the outer casing 256 of the upper body 26, as will be described in greater detail below.

The lever 22 of the handle 12 includes a lever body 262, the upper lever arm 48 extending upwardly from the lever body 262, and the trigger arm 50 extending downwardly from the lever body 262. The lever body 262 is pivotally coupled to the outer casing 256 at a joint 264. The joint 264 includes a cylindrical pivot pin 266 that extends through, and is positioned in, a set of holes 268 defined in the outer casing 256 of the upper body 26 and the lever body 262. A biasing element, illustratively embodied as a spring 270, is positioned between a bottom surface 272 of the lever body 262 and an inner surface 274 of the outer casing 256.

The lever release mechanism 56 of the handle 12 is embodied as a curved frame 280 and a plurality of teeth 282 defined in the top surface 284 of the lever body 262. As will be described in greater detail below, the curved frame 280 is moved into and out of engagement with the teeth 282 to permit or inhibit movement of the lever 22. The curved frame 280 has a top surface 286 and a bottom surface 288 positioned opposite the top surface 286. An opening 290 is defined in the top surface 286, and the curved frame 280 includes an inner wall 292 that extends downwardly from the opening 290. The inner wall 292 defines a slot 294, and the upper lever arm 48 of the lever 22 extends through that slot 294.

The curved frame 280 of the lever release mechanism 56 includes a catch 296 that extends from a lower tip 298 thereof. The catch 296 is configured to engage with the teeth 282 of the lever body 262. The curved frame 280 is pivotally coupled to the outer casing 256 at a joint 300 such that the catch 296 may be moved into and out of engagement with the teeth 282. The joint 300 includes a cylindrical pivot pin 302 that is received in a hole 306 defined in the outer casing 256 and a hole 308 defined in the curved frame 280. A biasing element, illustratively embodied as a spring 304, is positioned between the pin 302 and the bottom of the hole 308.

The lever release mechanism 56 also includes a button 310 that is positioned over the upper tip 312 of the curved frame 280. In the illustrative embodiment, the button 310 is molded over the upper tip 312 to form a single piece. It should be appreciated that in other embodiments the button 310 may be formed separately from the curved frame 280 and later attached thereto. The button 310 includes a contoured upper surface 314 configured to receive a fingertip of a user and a lower surface 316 positioned opposite the upper surface 314. A biasing element, illustratively embodied as a spring 318, is positioned between the bottom surface 320 and an inner surface 322 of the casing 256 to urge the curved frame 280 to pivot about the joint 300 such that the catch 296 is biased into engagement with the teeth 282.

In use, the catch 296 is biased into engagement with the teeth 282. The biased engagement of the catch 296 to the teeth 282 prevents the lever 22 from moving relative to the housing 20 along the longitudinal axis 58. However, when a predetermined amount of force is applied to the trigger arm 50, the bias of the spring 318 is overcome such that the upper lever arm 48 is moved along longitudinal axis 58 and the catch 296 is advanced stepwise along the teeth 282. When the user stops applying force to the trigger arm 50, the spring 318 urges the catch 296 into engagement with the teeth 282, thereby preventing additional movement of the lever 22.

Additionally, the catch 296 may be disengaged from the teeth by pressing down on the upper surface 314 of the button 310 of the lever release mechanism 56, thereby overcoming the bias of the spring 318 and causing the curved frame 280 to pivot about the joint 300. When the catch 296 is not engaged with the teeth 282, the lever 22 is permitted to move relative to the housing 20. If the no force is applied to the lever 22, the spring 270 positioned between the lever body 262 and the outer casing 256 urges the lever 22 to pivot about the joint 264, thereby moving the trigger arm 50 away from the outer surface 244 of the grip 30 and simultaneously moving the upper lever arm 48 along longitudinal axis 58 away from the closed end 44 of the channel 42. When the user releases the button 310, the spring 318 urges the curved frame 280 to pivot about the joint 300 such that the catch 296 is moved back into engagement with the teeth 282.

As described above, the upper body 26 of the multifunctional handle 12 also includes the mounting surface 32, which supports a surgical tool 14 when the surgical tool 14 is coupled to the handle 12. As shown in FIG. 2, the mounting surface 32 has an opening 330 extending transverse to the channel 42. A pair of sidewalls 332, 334 extends downwardly from the opening 330 to define a channel 336. The channel 336 includes an opening 338 defined in one wall 340 of the outer casing 256 and another opening 342 defined in the opposite wall 344. The channel 336 also has a bottom surface 346 extending the length thereof between the sidewalls 332, 334.

The locking mechanism 24, which secures each surgical tool 14 to the handle 12, includes a circular opening 350 defined in the bottom surface 346 of the channel 336, and a second opening 352 defined in the wall 340 of the outer casing 256. An aperture 354 extends inwardly from the opening 352, and a cylindrical passageway 356 extends downwardly from the opening 350 to the aperture 354, thereby connecting the channel 336 with the aperture 354.

The locking mechanism 24 also includes a locking bracket 358 positioned in the aperture 354. The locking bracket 358 has an end 362 positioned adjacent to the wall 344 of the outer casing 256 and an end 364 extending outwardly from the opening 352 in the wall 340. The locking bracket 358 also includes a rectangular body 360 having a flange 366 extending from the end 362 and another flange 380 extending from the end 364. The flange 366 of the body 360 includes an outer surface 368 facing the wall 344 of the outer casing 256 and a chamfered inner surface 370 positioned opposite the outer surface 368. A biasing element, which is embodied as a spring 372, is positioned between the outer surface 368 of the flange 366 and the wall 344.

As shown in FIG. 2, the rectangular body 360 of the locking bracket 358 also includes a lower sidewall 374 having a front surface 378. A pin 376 extending through the aperture 354 of the outer casing 256 is configured to engage with the front surface 378, as will be described in greater detail below. The other flange 380 of the body 360 has a button 382 secured thereto. In the illustrative embodiment, the button 382 is molded over the flange 380 to form a single piece. It should be appreciated that in other embodiments the button 382 may be formed separately from the flange 380 and later attached thereto. The button 382 includes a contoured outer surface 384, which is configured to receive a fingertip of a user. A user may depress the button 382 in the direction indicated by arrow 386 in FIG. 1.

As described above, the locking mechanism 24 of the handle 12 cooperates with the mounting bracket 70 to secure a surgical tool 14 (e.g., the resection guide 16 and the drill guide 18) to the handle 12. As shown in FIG. 1, the mounting bracket 70 includes a base 390 and a shaft 392 extending downwardly from the base 390. The shaft 392 has a notch 394 defined in an outer surface 396 thereof.

In use, when a surgical tool 14 is positioned on the mounting surface 32 of the handle 12, the base 390 of the mounting bracket 70 is received in the channel 336 of the outer casing 256. The shaft 392 of the mounting bracket 70 extends through the cylindrical passageway 356 such that the notch 394 is positioned in the aperture 354. The spring 372 urges the locking bracket 358 of the handle 12 into engagement with the mounting bracket 70 of the surgical tool 14 such that the chamfered surface 370 of the flange 366 is received in the notch 394 of the shaft 392. In that way, the surgical tool 14 is secured to the handle 12.

When a user depresses the button 382, the flange 366 is removed from the notch 394 as the locking bracket 358 is disengaged from the mounting bracket 70. The user may then remove the surgical tool 14 from the multifunctional handle 12. When the user releases the button 382 after the surgical tool 14 is removed, the spring 372 urges the locking bracket 358 to move along the aperture 354 toward the opening 352, thereby advancing the lower sidewall 374 of the locking bracket 358 into contact with the pin 376. When the sidewall 374 engages the pin 376, further movement by the locking bracket 358 is prevented.

Referring now to FIGS. 3A and 3B, the patella resection guide 16 is shown partially disassembled. As described above, the clamp 52 of the resection guide 16 includes the mounting bracket 70. The base 390 of the mounting bracket 70 is secured to the lower surface 68 of the body 60 of the clamp 52. The shaft 392 extends downwardly from the base 390, and the notch 394 is defined in the outer surface 396 thereof. As shown in FIG. 3A, the mounting bracket 70 is formed as a separate part, which is assembled to the clamp 52. It should be appreciated that in other embodiments the mounting bracket 70 may be formed as a single piece with the body 60 of the clamp 52.

As previously described, the slide arm 62 of the clamp 52 moves within the track 100 of the body 60 along the axis 140. The sidewalls 96, 98 define the track 100 in the body 60, and the track 100 includes a pair of grooves 400, 402 defined in the sidewalls 96, 98, respectively. Each of the grooves 400, 402 extends from the opening 102 defined in the inner wall 74 of the body 60 to the opening 104 defined in the outer wall 106.

The main body 108 of the slide arm 62 includes a pair of flanges 404, 406 extending outwardly therefrom. Each of the flanges 404, 406 is received in a corresponding one of the grooves 400, 402, as shown in FIG. 1. The flanges 404, 406 and grooves 400, 402 are sized such that the arm 62 may slide relative to the body 60 along the axis 140.

The range of motion of the slide arm 62 is limited by a stop 408. The stop 408 is illustratively embodied as a cylindrical pin 412 positioned in a hole 410 defined in the bottom surface 414 of the track 100. The pin 412 is received in a closed slot 416, which is defined in a lower surface 418 of the main body 108 of the slide arm 62. The slide arm 62 is permitted to slide relative to the body 60 until the pin 412 contacts one of the ends of the slot 416. The range of motion of the slide arm 62 is therefore limited by the length of the slot 416 and the position of the pin 412 in the bottom surface 414 of the track 100.

As shown in FIG. 3B, the resection guide 16 also includes the saw capture 64 that is configured to be removably coupled with the clamp 52. To that end, the saw capture 64 has the attachment mechanism 162, which, in the illustrative embodiment, includes the pair of mounting arms 164, 166 and the pair of mounting brackets 168, 170. The mounting arms 164, 166 are pivotally coupled to the rear portion of the frame 150 of the saw capture 64. Each of the mounting arms 164, 166 includes a base 420 that is pivotally coupled to the frame 150 at a joint 422. The joint 422 includes a pivot pin 424 that extends through, and is positioned in, a set of holes 426 defined in the frame 150 and the base 420.

Each of the mounting arms 164, 166 also includes a lever arm 428 extending outwardly from the base 420 and a sleeve 430 extending over a section of the lever arm 428. In the illustrative embodiment, the sleeve 430 is molded over the lever arm 428 to form a single piece. It should be appreciated that in other embodiments the sleeve 430 may be formed separately from the lever arm 428 and later attached thereto.

The sleeve 430 includes a contoured outer surface 432 configured to receive a fingertip of a user. A biasing element, illustratively embodied as a spring 434, is positioned between the lever arm 428 and a lower sidewall 436 of the frame 150.

Each of the mounting arms 164, 166 also includes a flange 438 extending outwardly from the base 420. An angle θ is defined between the flange 438 and the lever arm 428. In the illustrative embodiment, the angle θ is an obtuse angle. Additionally, as shown in FIG. 3, the flange 438 has an upper surface 440 that faces the frame 150. Each of the mounting arms 164, 166 also includes an inner sidewall 442. The inner sidewall 442 extends downwardly from the upper surface 440 of each flange 438 to define a notch 444 therein.

As shown in FIG. 3B, the attachment mechanism 162 of the saw capture 64 also includes the pair of mounting brackets 168, 170. Each of the mounting brackets 168, 170 includes a base 446 extending downwardly from the frame 150 to an end 448. A flange 450 extends inwardly from the end 448 of each base 446 toward the aperture 160 defined in the frame 150. It will be appreciated that in other embodiments the saw capture 64 may include additional or fewer brackets 168, 170.

As described above, the clamp 52 includes a number of predefined areas that are engaged by the attachment mechanism 162. In the illustrative embodiment, the outer wall 106 of the body 60 includes a plurality of undercuts 452. Each of the undercuts 452 is configured to receive one of the flanges 438 of the arms 164, 166 and the flanges 450 of the brackets 168, 170. As shown in FIG. 3B, the plurality of undercuts 452 include undercuts 454, 456 positioned on either side of the track 100 and undercuts 458, 460 positioned on either side of the jaw 78. When the saw capture 64 is secured to the body 60, the notch 444 in the flange 438 of the mounting arm 164 is received in the undercut 454 of the body 60 and the notch 444 in the flange 438 of the arm 166 is received in the undercut 456. Similarly, the flanges 450 of the brackets 168, 170 are received in undercuts 458, 460, respectively, when the saw capture 64 is secured to the body 60.

To assemble the resection guide 16, the user positions the saw capture 64 in front of and slightly above the body 60. Sliding the saw capture 64 relative to the body 60 toward the end 112 of the slide arm 62 engages the flanges 450 of the brackets 168, 170 with the undercuts 458, 460 positioned on either side of the jaw 78. When the brackets 168, 170 are seated in the undercuts 458, 460, the user may press on the contoured outer surface 432 of each of the mounting arms 164, 166. As the user presses on the mounting arms 164, 166, the arms 164, 166 pivot about their respective joints 422 to reposition the flanges 438.

The user may lower the rear portion of the saw capture 64 into contact with the upper surface 66 of the body 60 prior to releasing the arms 164, 166. When the user releases the mounting arms 164, 166, the springs 434 connected to the arms 164, 166 urge the arms to pivot about their respective joints 422. The flanges 438 move into engagement with the undercuts 454, 456 positioned on either side of the track 100, thereby securing the saw capture 64 to the clamp 52.

To detach the saw capture 64 from the body 60, the above-described process is repeated in reverse. That is, the user presses on the outer surface 432 of each of the mounting arms 164, 166 to cause the arms 164, 166 to pivot about their respective joints 422. As the arms 164, 166 are pivoted, the flanges 438 disengage from the undercuts 454, 456. The user may then lift the rear portion of the saw capture 64 above the upper surface 66 of the body 60 and slide the saw capture 64 relative to the body 60 to disengage the flanges 450 of the brackets 168, 170 from the undercuts 458, 460.

As shown in FIG. 3B, the frame 150 of the saw capture 64 also includes a plurality of lower walls 462 positioned around the outer perimeter of the aperture 160. Each of the lower walls 462 has a lower surface 464 that contacts the planar upper surface 66 of the clamp 52 when the saw capture 64 is coupled thereto. As will be described in greater detail below, the planar upper surface 66 of the clamp 52, the lower walls 462 of the saw capture 64, and the planar lower surface 154 of the saw capture 64 define a plurality of cutting slots 466 therebetween. Each of the cutting slots 466 is sized to receive a cutting saw blade of a surgical saw.

As described above, the resection guide 16 also includes a height gauge 172. The base 174 of the height gauge 172 has a cylindrical body 470 that extends upwardly from the frame 150, and the body 470 includes an upper surface 472. The upper surface 472 has an opening 474 defined therein, and the body 470 includes an inner wall 476 extending downwardly from the opening 474. The inner wall 476 cooperates with a bottom surface 480 to define an aperture 478.

As shown in FIG. 3B, the stylus arm 176 includes a mounting head 482 and a plug 484. The plug 484 includes an upper body 486 and a shaft 488 extending downwardly from the upper body 486. The mounting head 482 is positioned below the upper body 486 of the plug 484 and over the opening 474 of the base 174. A spacer 490 is positioned in the aperture 478 in contact with the lower surface 178 of the stylus arm 176. A bellevelle washer 494 is positioned between the spacer 490 and the bottom surface 480 of aperture 478.

Each of the mounting head 482, spacer 490, and washer 494 includes a through hole 496 that receives the shaft 488 of the plug 484. A cylindrical pin 498, which is positioned in holes (not shown) defined in the inner wall 476 of the body 470 and the lower end of the shaft 488, secures the stylus arm 176 to the base 174 of the height gauge 172. The stylus arm 176 is free to rotate about an axis 500 defined by the shaft 488.

As described above, the lower surface 178 of the stylus arm 176 is configured to be located a predetermined height above the planar upper surface 66 of the clamp 52 when the saw capture 64 is coupled thereto. The predetermined height corresponds to the amount of bone to be removed during the patella resection, as will be described in greater detail below. In the illustrative embodiment, the predetermined height is approximately nine millimeters. It will be appreciated that in other embodiments the predetermined height may be lesser or greater according to the bony anatomy of the patient. It will also be appreciated that in other embodiments the height gauge 172 may be configured such that the height can be adjusted intra-operatively.

Referring now to FIG. 4, the patella drill guide 18 is shown partially disassembled. As described above, the patella drill guide 18 includes the support bracket 180 and the drill bracket 182, which moves within the track 200 of the support bracket 180. The sidewalls 196, 198 define the track 200 in the support bracket 180, and the track 200 includes a pair of grooves 510, 512 defined in the sidewalls 196, 198, respectively. Each of the grooves 510, 512 extends from the opening 202 defined in the end 204 of the support bracket 180 to the opening 206 defined in the opposite end 208.

The slide frame 210 of the drill bracket 182 includes a pair of flanges 514, 516 extending outwardly therefrom. Each of the flanges 514, 516 is received in a corresponding one of the grooves 400, 402, as shown in FIG. 1. The flanges 514, 516 and the grooves 510, 512 are sized such that the drill bracket 182 may slide relative to the support bracket 180.

The range of motion for the drill bracket 182 is limited by a stop 518. The stop 518 is illustratively embodied as a cylindrical pin 522 positioned in a hole 520 defined in the bottom surface 524 of the track 200. The pin 522 is received in a closed slot 526, which is defined in a lower surface 528 of the slide frame 210 of the drill bracket 182. The drill bracket 182 is permitted to slide relative to the support bracket 180 until the pin 522 contacts one of the ends of the slot 526. The range of motion for the drill bracket 182 is therefore limited by the length of the slot 526 and the position of the pin 522 in the bottom surface 524 of the track 100.

As shown in FIG. 4, the stationary arm 190 of the drill guide 18 has a body 530 that extends upwardly from the upper surface 188 of the support bracket 180. The body 530 includes the backing plate 192, which has a planar side surface 532. The planar side surface 532 of the plate 192 has a circular opening 534 defined in an upper end 536 of the body 530. The backing plate 192 also includes an inner wall 538 that extends inwardly from the circular opening 534. The inner wall 538 defines an aperture 540 through the body 530. A plurality of teeth 542 are positioned in the side surface 532 at equidistant points around the outer circumference of the opening 534.

The moveable arm 212 of the drill bracket 182 has a body 550 that extends upwardly from the upper surface 214 of the slide frame 210. The body 550 includes the drill plate 222, which includes plurality of guide holes 560 that are used to guide the drilling operations performed on the resected patella. The drill plate 222 has a planar side surface 552 that faces the side surface 532 of the stationary arm 190. The side surface 552 of the drill plate 222 has a plurality of circular openings 554, and the drill plate 222 includes an inner wall 558 that extends inwardly from each of the circular opening 554.

Each inner wall 558 defines one of the guide holes 560 through the drill plate 222. Each of the openings 554 and the guide holes 560 are sized to receive a surgical drill bit. In the illustrative embodiment, the drill plate 222 includes three guide holes 560 that are arranged in a triangular pattern; it should be appreciated that in other embodiments the drill plate 222 may include additional or fewer guide holes shaped and sized to receive an appropriate surgical drill bit. A plurality of teeth 562 are positioned in the side surface 552 adjacent to the openings 554.

The body 550 of the drill bracket 182 also includes an additional opening 564 positioned below the drill plate 222 at a lower end 566 thereof. The body 550 includes another inner wall 568 that extends inwardly from the opening 564 and defines another aperture 570 through the body 550. The aperture 570 has a first section 572 that extends from the opening 564 and a second section 574 connected to the first section 572. The second section 574 has a diameter greater than the first section 572 such that the aperture 570 is "stair-stepped."

As shown in FIG. 4, the drill guide 18 also includes the compression gasket 184 pivotally coupled to the moveable arm 212. In the illustrative embodiment, the gasket 184 is formed from an elastomeric material such as rubber, but it will be appreciated that in other embodiments the gasket 184 may be formed from a polymeric material. The gasket 184 has a body 580 extending from a lower end 582 to an upper end 584. A plug 586 extends from the lower end 582 of the gasket 184. The plug 586 is received in the aperture 570 of the drill bracket 182 and is configured to secure the gasket 184 to the drill bracket 182.

To do so, the plug 586 has a main shaft 588 that is positioned in the first section 572 of the aperture 570. A rim 590, which extends outwardly from the main shaft 588, is positioned within the second section 574 of aperture 570. Because the diameter of the rim 590 is greater than the diameter of the first section 572, the plug 586 is maintained in the aperture 570, thereby securing the gasket 184 to the moveable arm 212.

The body 580 of the gasket 184 also has cylindrical plugs 592 extending from the upper end 584 of the gasket 184. The plugs 592 are arranged on the body 580 such that each plug 592 may be received in a corresponding guide hole 560 of the drill plate 222 to secure the gasket 184 in place. The body 580 also includes holes 576 (see FIG. 16) configured to receive the teeth 562 extending from the side surface 552 of the drill plate 222.

The body 580 of the gasket 184 further includes a tab 594 extending from the upper end 584. The tab 594 includes a pair of contoured surfaces 596 configured to receive the fingertips of the user. In use, the user may grip the surfaces 596 to rotate the gasket 184 relative to the arm 212, thereby moving the gasket 184 out of the drilling path when preparing to drill holes in a resected patella. In that way, the plugs 592 of the gasket 184 may be moved into and out of the guide holes 560 of the drill plate 222.

The cylindrical plugs 592 of the gasket 184 are formed on a side surface 598 of the body 580. The body 580 includes another side surface 600 that is positioned opposite the side surface 598. As shown in FIG. 4, the side surface 600 is concave and is configured to receive a portion of an implantable patella prosthetic component, as will be described in greater detail below. The side surface 600 also includes an opening 602 defined in the center thereof, and the opening 602 extends through both surfaces 598, 600.

Figure 5:
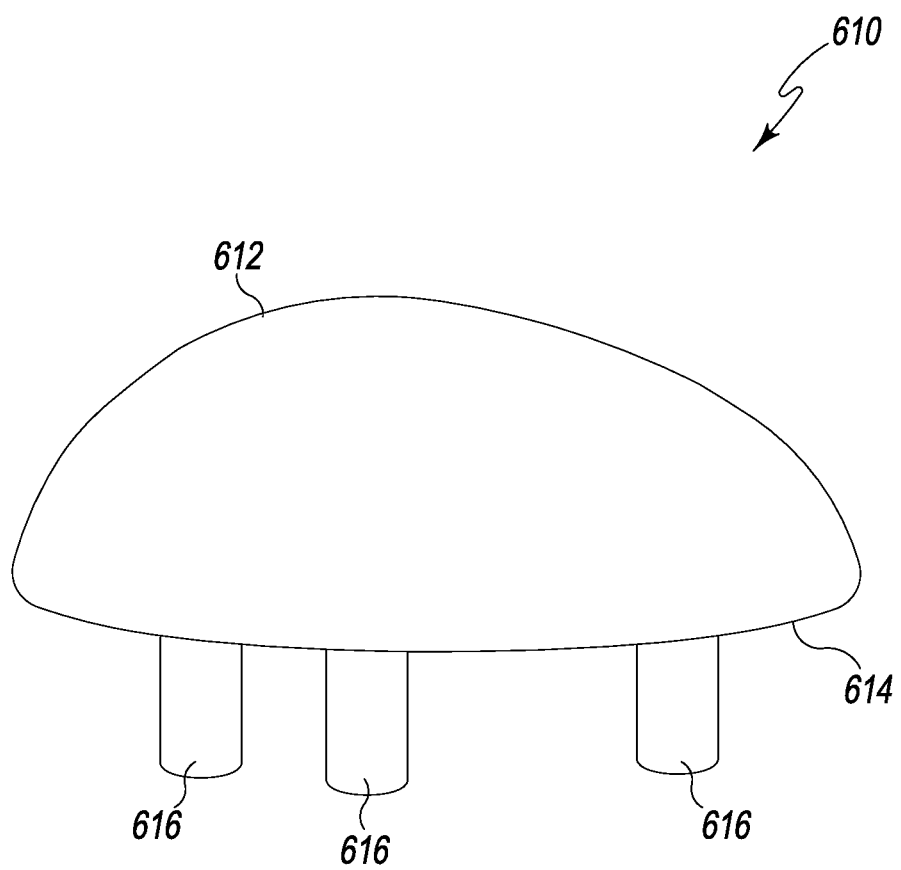
FIG. 5 is a side elevation view of a patella prosthetic component that may be attached to a patient's resected patella by use of the orthopaedic surgical instrument assembly of FIG. 1.

Referring now to FIG. 5, there is shown an illustrative patella prosthetic component 610 that may be attached to a patient's resected patella by use of the surgical instrument assembly 10. The component 610 includes a posterior bearing surface 612 configured to articulate with the condylar surfaces a femoral component (not shown). The component 610 also includes a flat anterior surface 614 having a number of fixation members, such as pegs 616, extending away therefrom. The pegs 616 are configured to be implanted into a surgically-prepared posterior surface of the resected patella, as will be described in greater detail below. In such a way, the posterior bearing surface 612 of the components 610 faces toward the femoral component, thereby allowing the posterior bearing surface 612 to articulate with the femoral condyle surfaces during flexion and extension of the patient's knee.

Figure 6A:
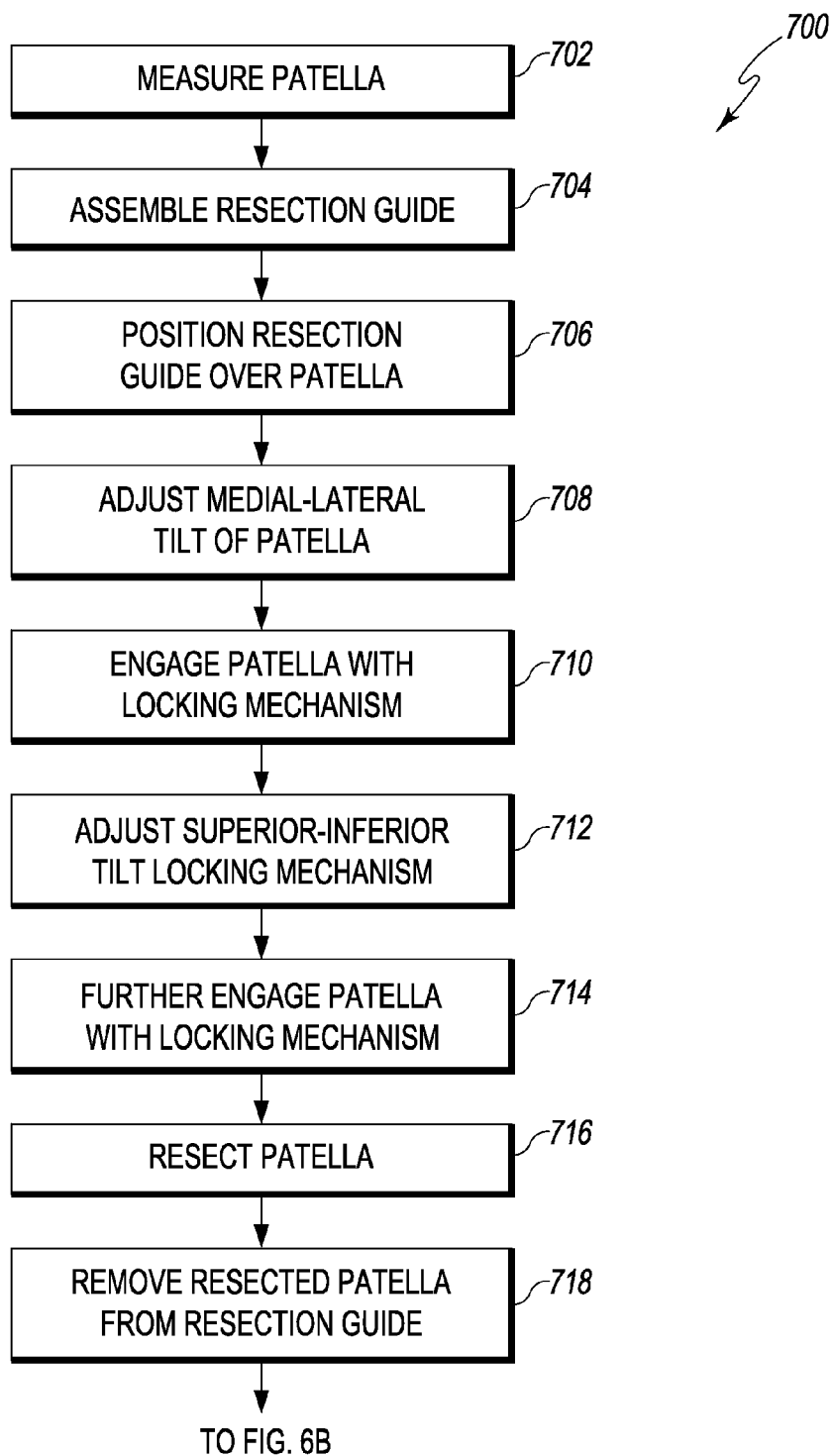
FIGS. 6A and 6B are simplified flow charts of one embodiment of a procedure for using the orthopaedic surgical instrument assembly of FIGS. 1-4.
Figure 15:
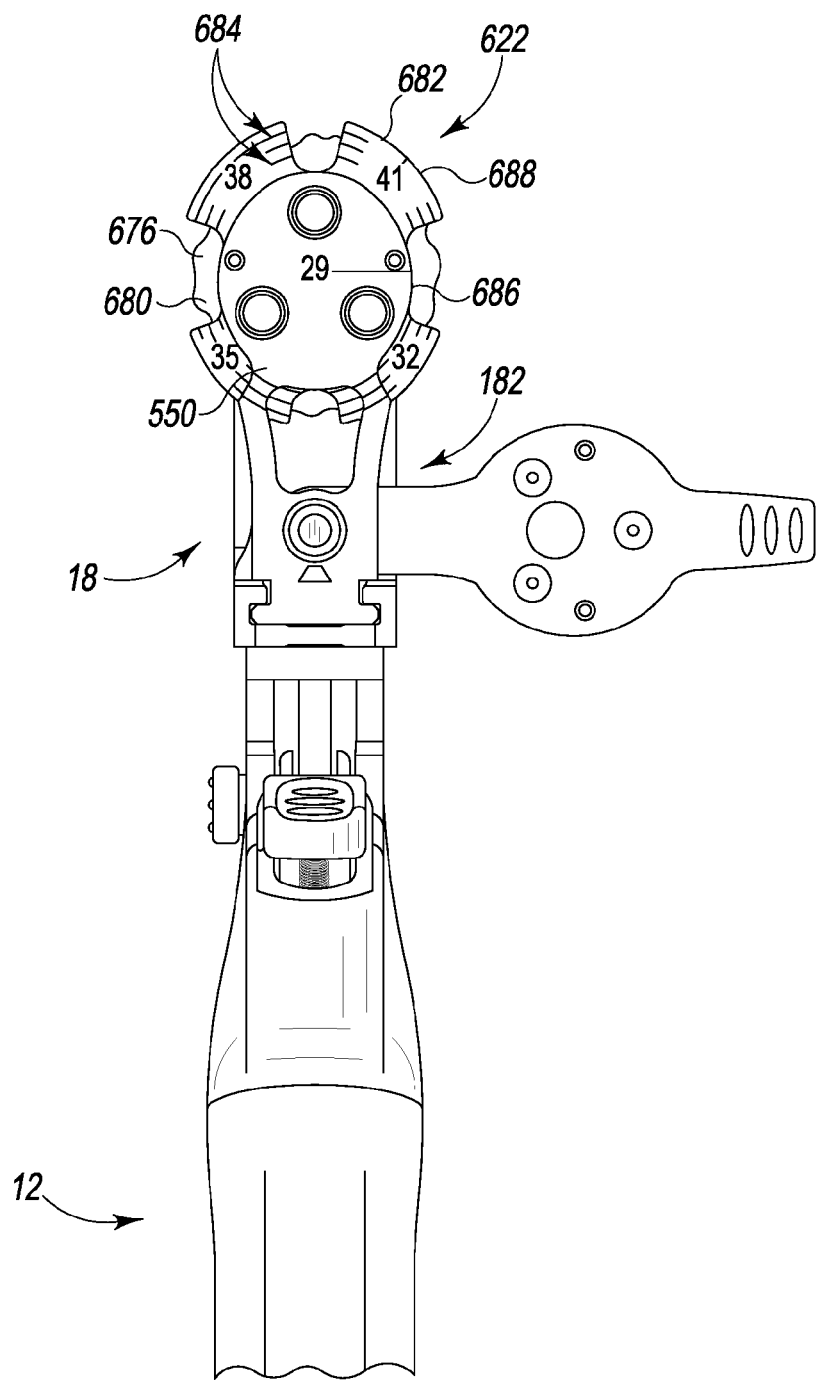
FIG. 15 is a view of the patella drill guide and handle assembly of FIG. 14 with the resected patella positioned in the patella drill guide.
Figure 16:
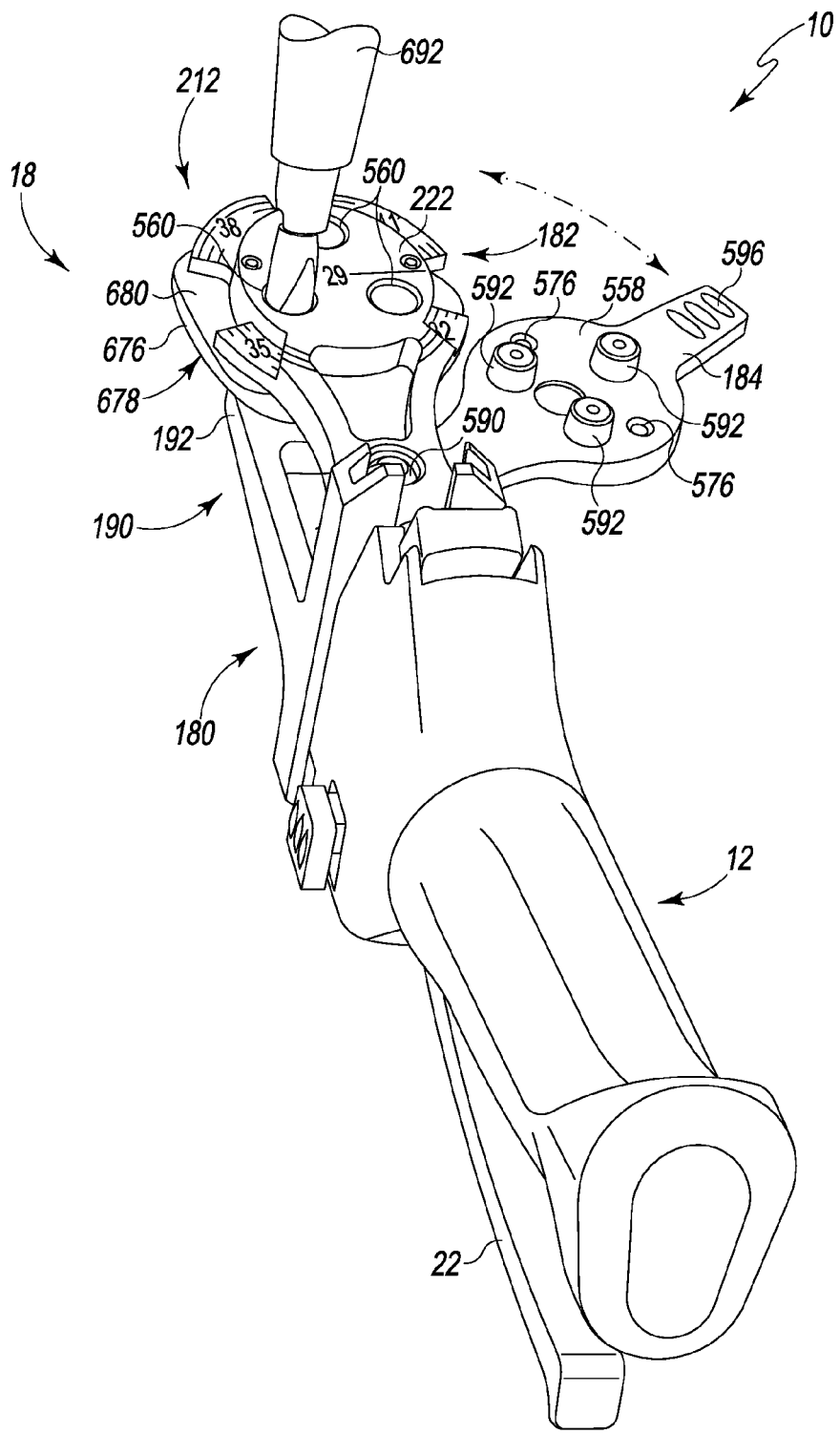
FIG. 16 is a perspective view of the patella drill guide and handle assembly of FIG. 14 engaged with the resected patella and showing a surgical drill bit inserted in a guide hole of the patella drill guide.
Figure 17:
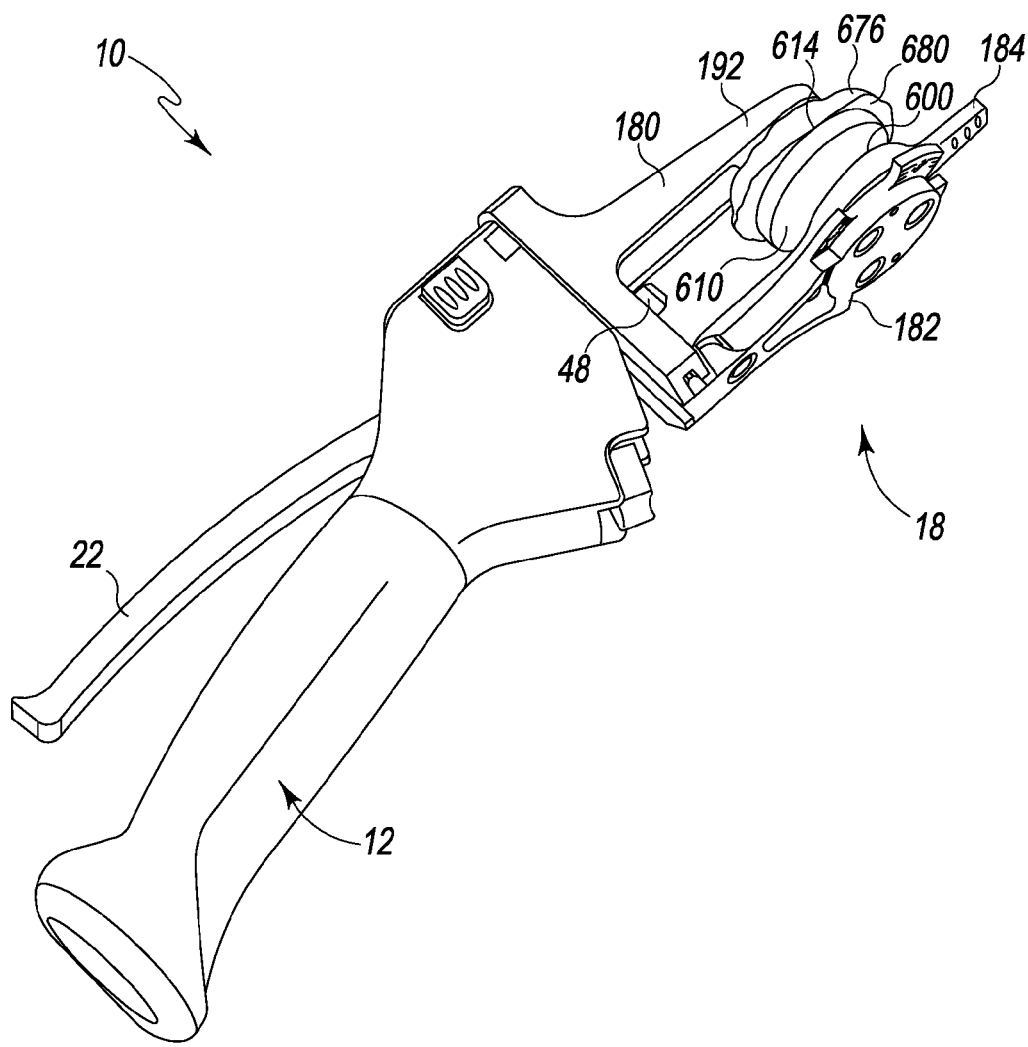
FIG. 17 is a perspective view of the patella drill guide and handle assembly of FIG. 14 showing the patella drill guide engaged with the resected patella and the patella prosthetic component.

In operation, the orthopaedic surgical instrument assembly 10 is utilized to surgically prepare a patient's patella for implantation of a patella prosthetic component, such as the patella prosthetic component 610, during the performance of an orthopaedic surgical procedure like that shown in FIGS. 6A & B. As shown in FIGS. 6-13, the patient's patella is first resected by use of, for example, a surgical saw. Thereafter, a patella prosthetic component is selected, and guide holes are drilled into the resected patella, as shown in FIGS. 15 and 16. The patella prosthetic component may be secured to the resected patella, as shown in FIG. 17.

Referring now to FIG. 6A, an illustrative orthopaedic surgical procedure 700 using the surgical instrument assembly 10 is shown. In block 702, the surgeon utilizes a pair of calipers or other measuring device to measure the anterior-posterior thickness of the patient's natural patella and calculate the level of bone resection. The amount of bone removed approximately corresponds to the thickness of the patella prosthetic component. In that way, after the patella prosthetic component is attached to the resected patella, the total thickness of the resected patella and the patella prosthetic component should be about the same as the thickness of the natural patella.

Figure 8:
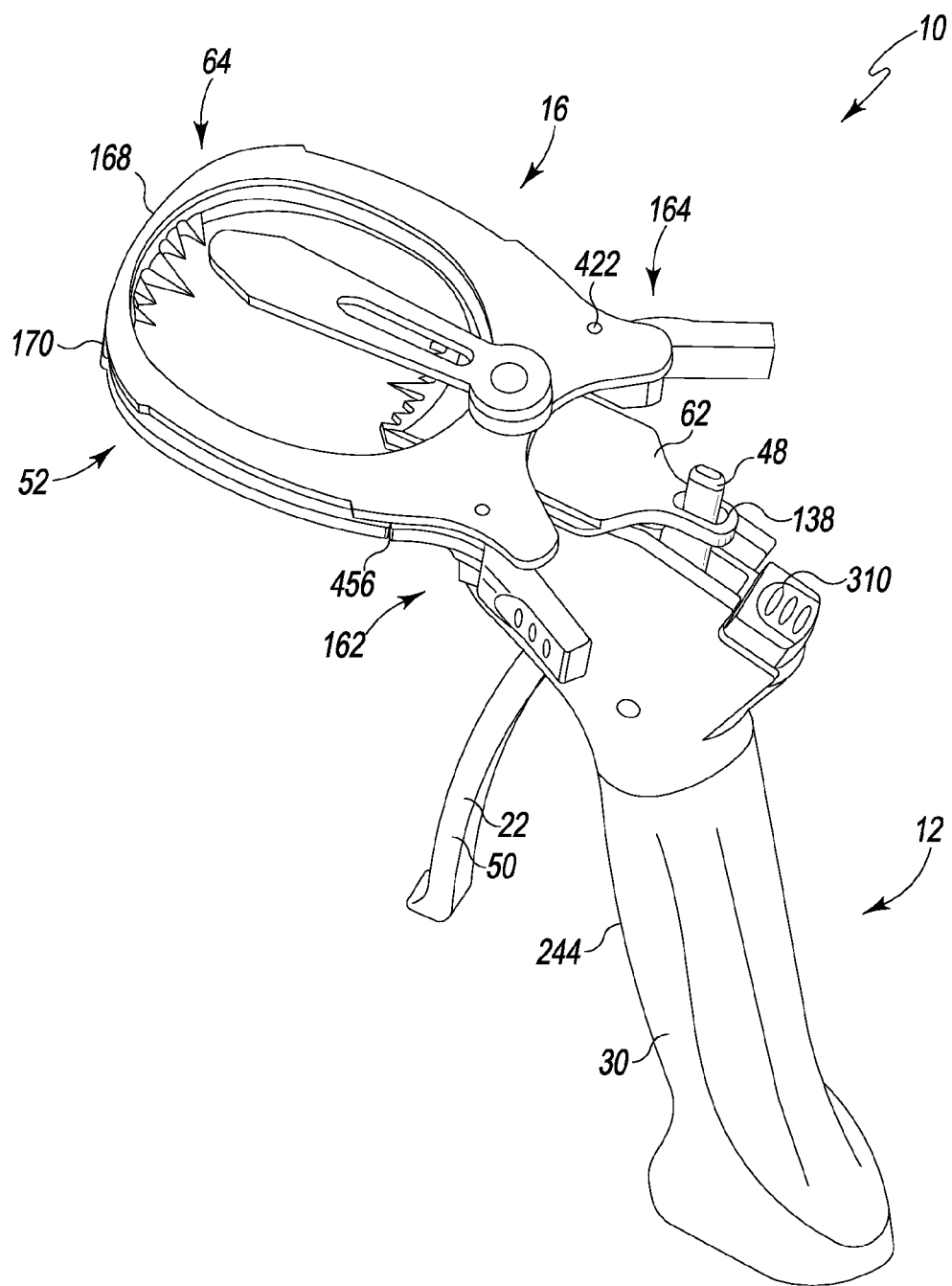
FIG. 8 is a perspective view similar to FIG. 7 showing the saw capture attached to the patella clamp of the patella resection guide.

In block 704 of the procedure 700, the surgeon assembles the resection guide 16 and attaches the resection guide 16 to the multifunctional handle 12, as discussed previously in regard to FIGS. 1-3. The surgeon may begin by attaching the saw capture 64 to the clamp 52 before attaching the assembled resection guide 16 to the handle 12. Alternatively, as shown in FIGS. 7 and 8, the surgeon may first attach the patella clamp 52 to the handle 12 prior to attaching the saw capture 64. It should also be appreciated that in some embodiments the patella clamp 52 may be used without the saw capture 64.

To attach the clamp 52 to the handle 12, the surgeon aligns the mounting bracket 70 of the clamp 52 with the channel 336 defined in the mounting surface 32 of the handle 12. The surgeon also aligns the slot 138 defined in the clamp 52 with the upper lever arm 48 of the handle 12. The clamp 52 is then lowered onto the mounting surface 32 of the handle 12 such that the base 390 of the bracket 70 is received in the channel 336 and the upper lever arm 48 is received in the slot 138, as shown in FIG. 7. As described above, the locking mechanism 24 engages with the mounting bracket 70 to secure the patella clamp 52 to the multifunctional handle 12.

Referring now to FIG. 8, the saw capture 64 is attached to the clamp 52 to complete the assembly of the resection guide 16. To do so, the surgeon engages the mounting brackets 168, 170 of the saw capture 64 with the undercuts 458, 460 of the clamp 52. When the brackets 168, 170 are seated in the undercuts 458, 460, the user may press inwardly on the mounting arms 164, 166 such that the arms 164, 166 pivot about their respective joints 422. While pressing inwardly on the mounting arms 164, 166, the surgeon lowers the rear portion of the saw capture 64 into contact with clamp 52 and releases the mounting arms 164, 166. The springs 434 connected to the arms urge the arms 164, 166 to pivot about their respective joints 422 such that the mounting arms 164, 166 engage with the undercuts 454, 456 of the clamp 52, thereby securing the saw capture 64 to the clamp 52.

Returning to FIG. 6A, the resection guide 16 is placed over the patient's patella such that the patella is positioned between the jaws 78, 114 in block 706 of the procedure 700. To accommodate patellas of varying sizes, the surgeon may increase the space between the jaws 78, 114. To do so, the surgeon operates the lever release mechanism 56 to move the jaw 114 away from the jaw 78.

As described above, pressing down on the button 310 of the lever release mechanism 56 disengages the catch 296 from the teeth 282 formed on the lever 22. When the catch 296 is not engaged with the teeth 282, the spring 270 urges the lever 22 to pivot, thereby moving the trigger arm 50 away from the outer surface 244 of the grip 30 and simultaneously moving the upper lever arm 48 away from the closed end 44 of the channel 42. As the lever arm 48 moves away from the closed end 44, the lever arm 48 acts on the inner wall 136 of the slide arm 62 to move the jaw 114 away from the stationary jaw 78. When the space between the jaws 78, 114 is large enough to fit the patient's patella, the surgeon releases the button 310, the spring 318 urges the catch 296 back into engagement with the teeth 282, thereby preventing additional movement of the slide arm 62 and hence the jaw 114.

Figure 9:
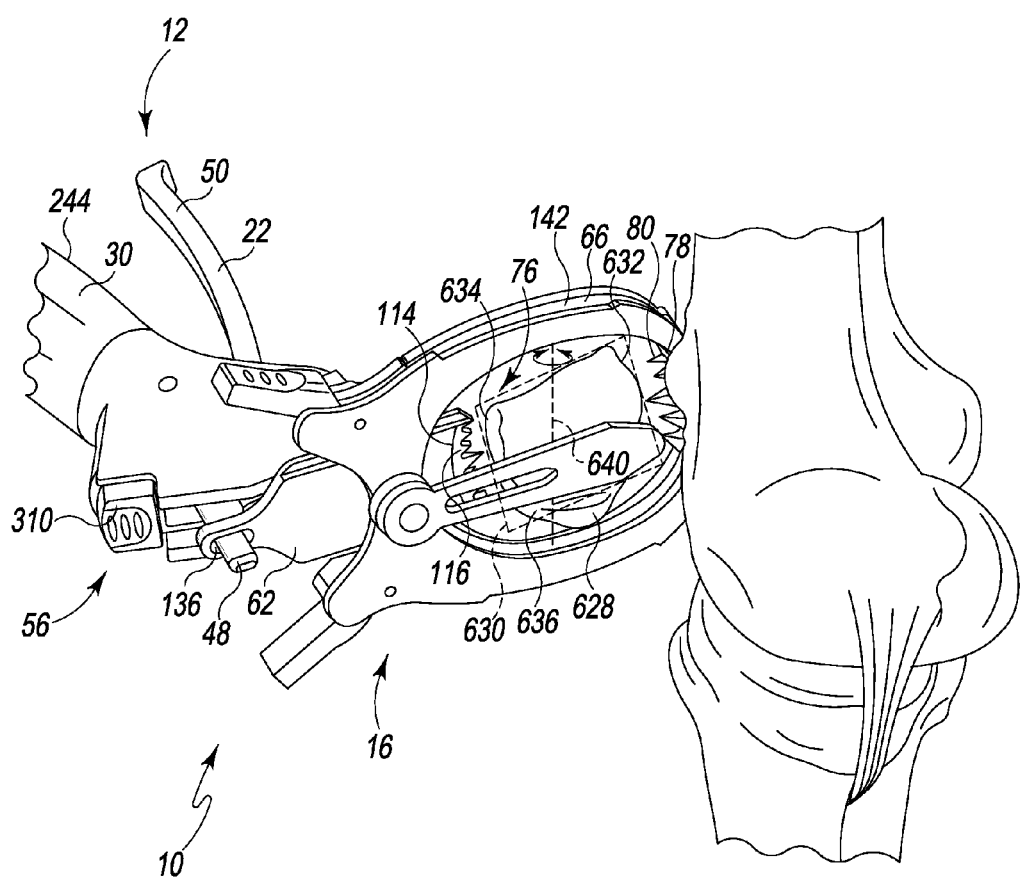
FIG. 9 is a perspective view of the orthopaedic surgical instrument assembly of FIG. 1 showing a patient's patella positioned within the patella resection guide.

Referring now to FIG. 9, there is shown an illustrative embodiment in which the resection guide 16 has been positioned over a patient's natural patella 630. The patella 628 is positioned in the aperture 76 of the resection guide 16. In that position, the stationary jaw 78 of the resection guide 16 is positioned adjacent to the lateral margin 632 of the patella 628, and the movable jaw 114 is positioned adjacent to the medial margin 634 of the patella 628. However, the teeth 80, 116 of the jaws 78, 114 are initially spaced apart from, and out of contact with, the patella 628.

Figure 10:
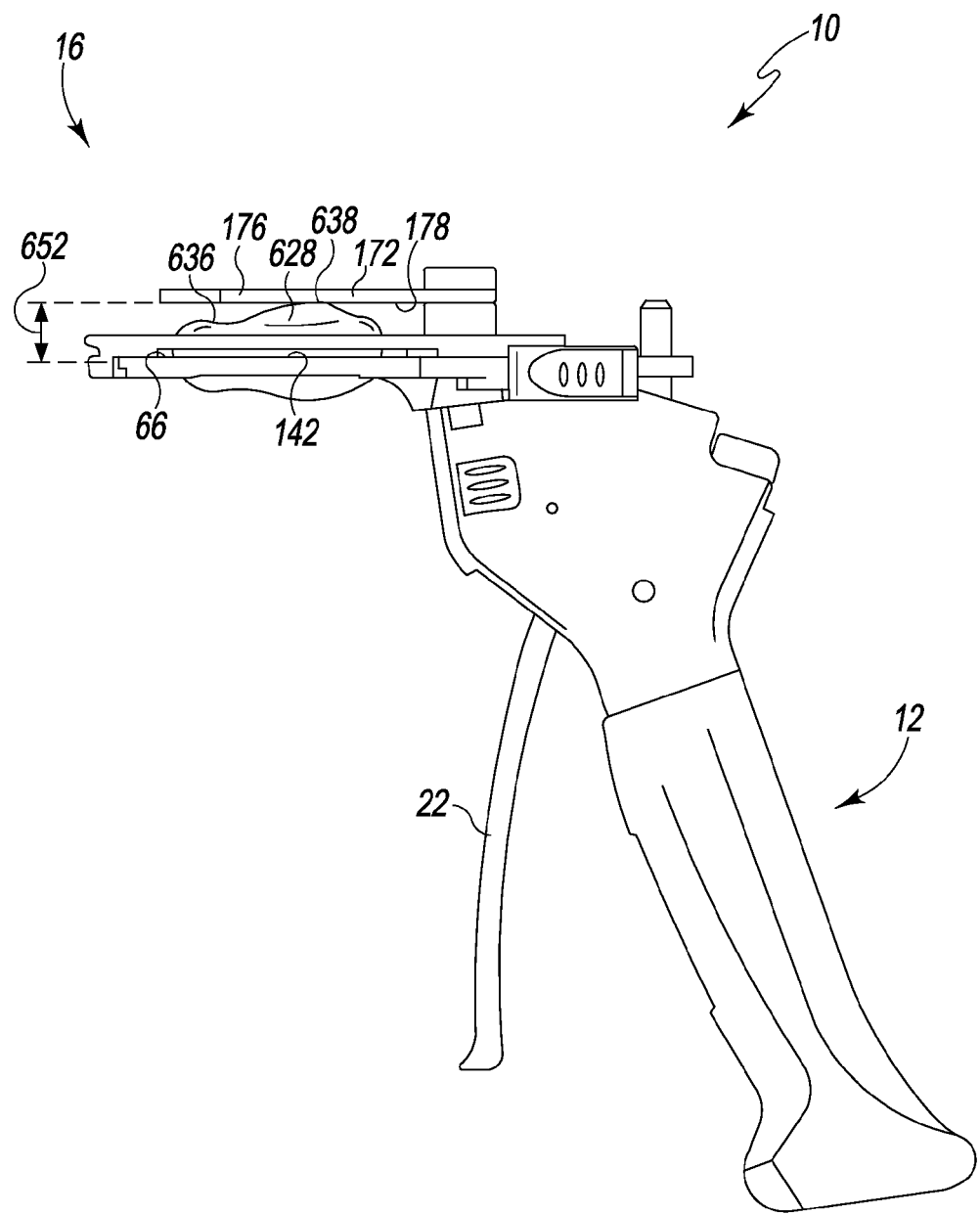
FIG. 10 is a side elevation view of the orthopaedic surgical instrument assembly of FIG. 1 showing of the patella positioned within the patella resection guide and in contact with the height gauge of the patella resection guide.

The posterior surface 636 of the patella 628 is placed in contact with the height gauge 172, as best seen in FIG. 10. As described above, the lower surface 178 of the stylus arm 176 of the height gauge 172 is located at a predetermined height 652 above the planar upper surface 66. Because the upper surface 66 defines the resection plane 142, the predetermined height corresponds to the amount of bone to be removed during the patella resection. If too much bone is removed during the resection, the risk of fracture may be increased. To reduce that risk, the surgeon places the lower surface 178 in contact with the posterior-most point 638 of the patella 628.

It should be appreciated that in other embodiments the surgeon may rotate the stylus arm 176 such that the height gauge 172 is moved out of the way, which allows the surgeon to further adjust the position of the patella 628 within the resection guide 16. Additionally, in other embodiments, the height gauge 172 may be adjustable so that the surgeon may change the height of the stylus arm 176 relative to the upper surface 66 intraoperatively. It will be further appreciated that in some embodiments the height gauge 172 may be omitted from the assembly 10.

Returning to FIG. 6A, the surgeon may adjust the medial-lateral tilt of the patella 628 within the resection guide 16 in block 708 of the procedure 700. The term "medial-lateral tilt" is defined herein as the angle defined between the resection plane of the resection guide and a bisecting reference plane extending through a lateral margin and a medial margin of the patella. In the illustrative embodiment, the medial-lateral tilt of the patella 628 is set to approximately zero.

For example, to adjust the medial-lateral tilt of the patella 628, the surgeon may rotate the patella 628 about an axis 640 extending in the superior-inferior direction through the patella 628. As shown in FIG. 9, a reference plane 630 defined by a lateral margin 632 and a medial margin 634 extends though the patella 628. In the illustrative embodiment, the medial-lateral tilt is set when the reference plane 630 is aligned with the resection plane 142 so that the angle defined therebetween is approximately zero. It should be appreciated that the degree or amount of rotation depends on the bony anatomy of the particular patient. After adjusting the medial-lateral tilt of the patella 628, the procedure 700 continues to block 710.

In block 710 of the procedure 700, the surgeon locks the medial-lateral tilt of the patella 628. To do so, the surgeon operates the lever 22 to move the jaw 114 to engage the patella 628 with the elongated tooth 82 of the jaw 78 and the elongated tooth 118 of the jaw 114. As described above, the upper lever arm 48 is advanced linearly toward the closed end 44 of the channel 42 when a predetermined amount of force is applied to the trigger arm 50 in the direction indicated by arrow 54. The upper lever arm 48 acts on the inner wall 136 of the slide arm 62 to move the slide arm 62 along the axis 140. As the slide arm 62 moves, the jaw 114 advances toward the stationary jaw 78 and the patella 628.

As the jaw 114 advances toward the stationary jaw 78 and the patella 628, the elongated tooth 82 of the jaw 78 engages the lateral margin 632 of the patella 628 and the elongated tooth 118 of the jaw 114 engages the medial margin 634. When the tips 86, 122 of the teeth 82, 118 are sufficiently embedded in the patella 628, the surgeon stops applying pressure to the lever 22. In that position, which is illustratively shown in FIG. 11, the remaining teeth 80, 116 of the jaws 78, 114 are spaced apart from the patella 628. With the teeth 82, 118 embedded in the patella 628, rotation of the patella 628 about the axis 640 is prevented and the medial-lateral tilt of the patella 628 is locked.

In block 712 of the procedure 700, the surgeon may adjust the superior-inferior tilt of the patella 628. The term "superior-inferior tilt" is defined herein as the angle defined between the resection plane of the resection guide and a bisecting reference plane extending through a superior margin and an inferior margin of the patella. In the illustrative embodiment, the superior-inferior tilt of the patella 628 is set to approximately zero to ten degrees.

Figure 11:
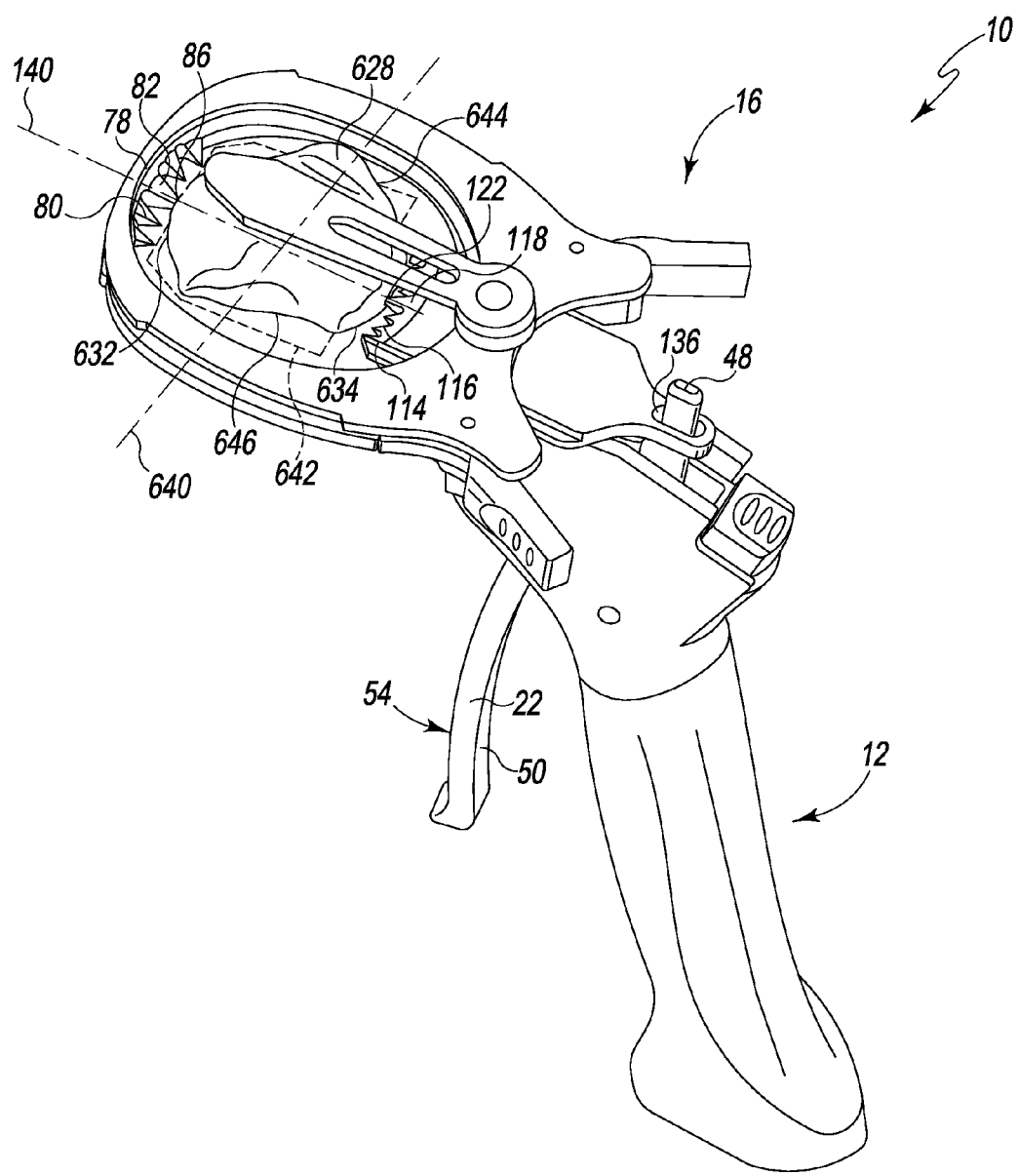
FIG. 11 is a perspective view similar to FIG. 9 showing the patella engaged by a locking mechanism of the patella resection guide.
Figure 12:
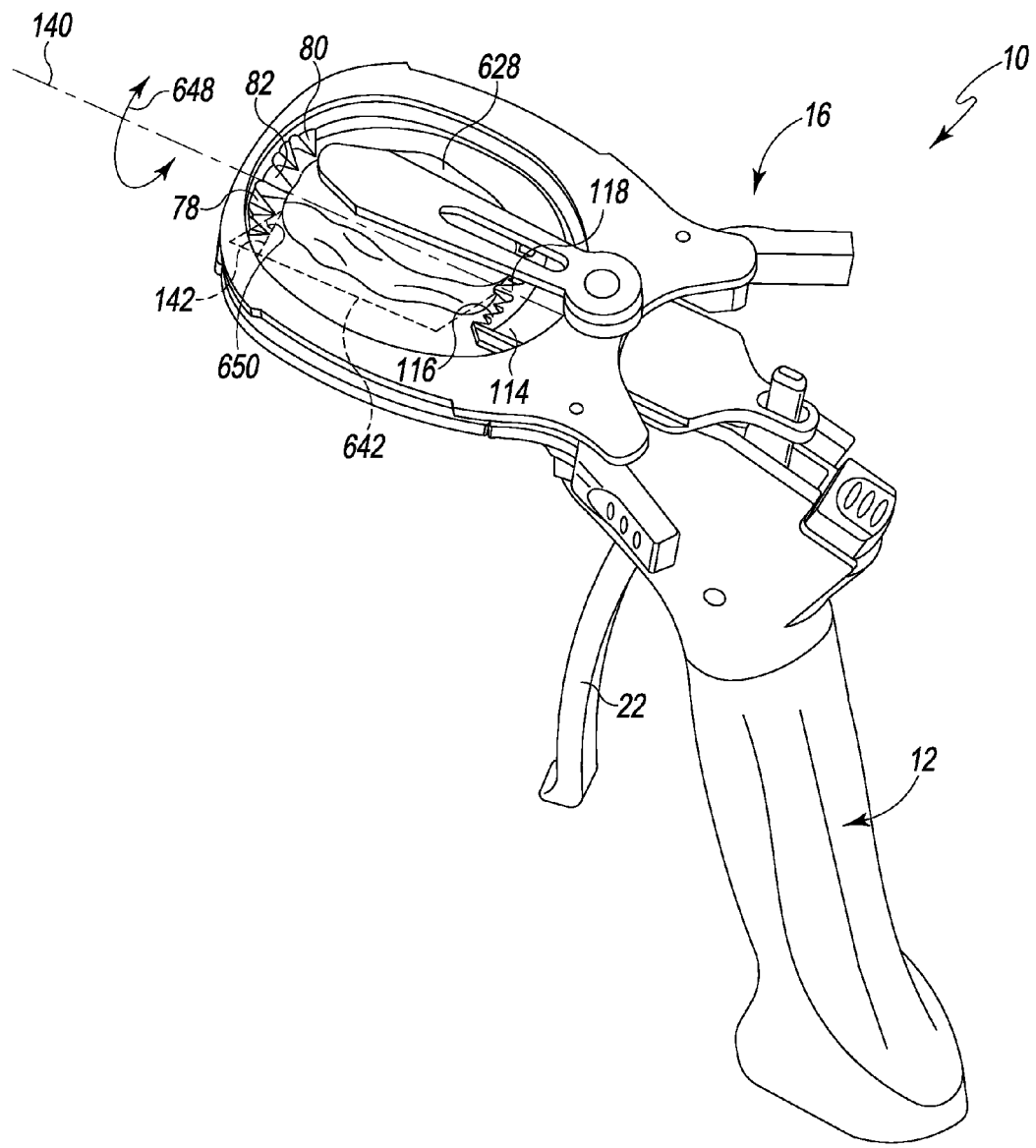
FIG. 12 is a perspective view similar to FIG. 9 showing the patella rotated about a medial-lateral axis within the patella resection guide.

For example, to adjust the superior-inferior tilt of the patella 628, the surgeon may rotate the patella 628 about an axis 140 extending in the medial-lateral direction through the patella 628. Because the patella 628 is engaged only by the teeth 82, 116 of the resection guide 16, the surgeon may rotate the patella 628 about the axis 140 in either direction indicated by arrow 648. As shown in FIG. 11, a reference plane 642 defined by a superior margin 644 and an inferior margin 646 of the patella 628 extends though the patella 628. As the patella 628 is rotated, an angle 650 is defined between the reference plane 642 and the resection plane 142, as shown in FIG. 12. The magnitude of the angle 650 corresponds to the superior-inferior tilt of the patella 628. In the illustrative embodiment, the patella 628 is rotated until the angle 650 has a magnitude of approximately zero to ten degrees. It should be appreciated that the degree or amount of rotation depends on the bony anatomy of the particular patient. After adjusting the superior-inferior tilt of the patella 628, the procedure 700 continues to block 714.

Figure 13:
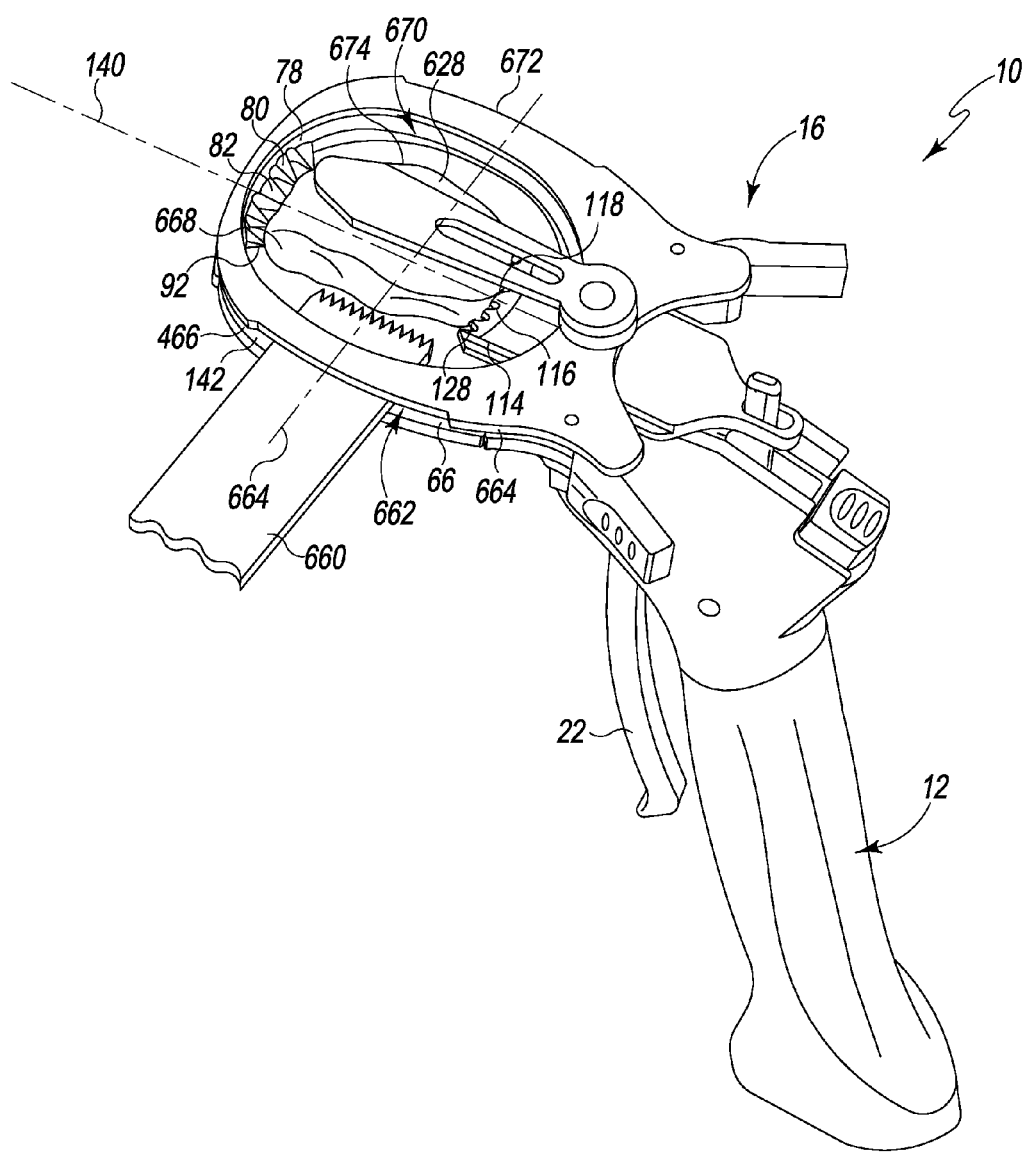
FIG. 13 is a perspective view similar to FIG. 9 showing the patella clamped by another locking mechanism of the patella resection guide and a cutting saw blade entering a cutting slot of the patella resection guide.

In block 714 of the procedure 700, the surgeon locks the superior-inferior tilt of the patella 628. To do so, the surgeon operates the lever 22 to move the jaw 114 and engage the patella 628 with the remaining teeth 80, 116 of the jaws 78, 114. When the tips 92, 128 of the remaining teeth 80, 116 are sufficiently embedded in the patella 628, the surgeon stops applying pressure to the lever 22. With the teeth 80, 116 embedded in the patella 628, further rotation of the patella 628 about the axes 140, 640 is prevented and both the medial-lateral tilt and the superior-inferior tilt of the patella 628 are locked, as shown in FIG. 13.

After the patella 628 is locked in block 714, the surgical procedure 700 shown in FIG. 6A continues to block 716 in which the patella is resected. To do so, the surgeon inserts a cutting saw blade 660 into one of the cutting slots 466 defined between the planar upper surface 66 of the clamp 52, the lower walls 462 of the saw capture 64, and the planar lower surface 154 of the saw capture 64. As shown in FIG. 13, the surgeon may insert the cutting saw blade 660 into the cutting slot 662 formed on the side 664 of the resection guide 16 corresponding to the superior side 668 of the patella 628. The cutting slot 662 defines an axis 664 extending orthogonal to the axis 140 defined by the teeth 82, 118. The blade 660 passes through the cutting slot 662 and contacts the superior side 668 of the patella 628.

Following the resection plane 142 defined by the upper surface 66 of the clamp 52, the surgeon may perform the resection cut on the patient's patella by moving the saw blade 660 back and forth within the cutting slot 662. As the blade 660 cuts through the patella, another cutting slot 670 positioned opposite the cutting slot 662 receives the blade 660. As shown in FIG. 13, the cutting slot 670 is positioned on the side 672 of the resection guide 16 corresponding to the inferior side 674 of the patella 628. After the patella 628 is resected, a remnant of the patella 628 (hereinafter referred to as the resected patella 676) is held between the jaws 78, 114 of the patella resection guide 16.

As described previously, it should be appreciated that in other embodiments the saw capture 64 may be omitted. In such embodiments, the surgeon places the cutting saw blade 660 in contact with the upper surface 66 and maintains that contact throughout the resection procedure.

Returning to FIG. 6A, the procedure 700 continues to block 718 in which the surgeon removes resected patella 676 from the resection guide 16. To do so, the surgeon again operates the lever release mechanism 56 to move the jaw 114 away from the jaw 78 and withdraw the teeth 80, 116 from the resected patella 676.

Figure 6B:
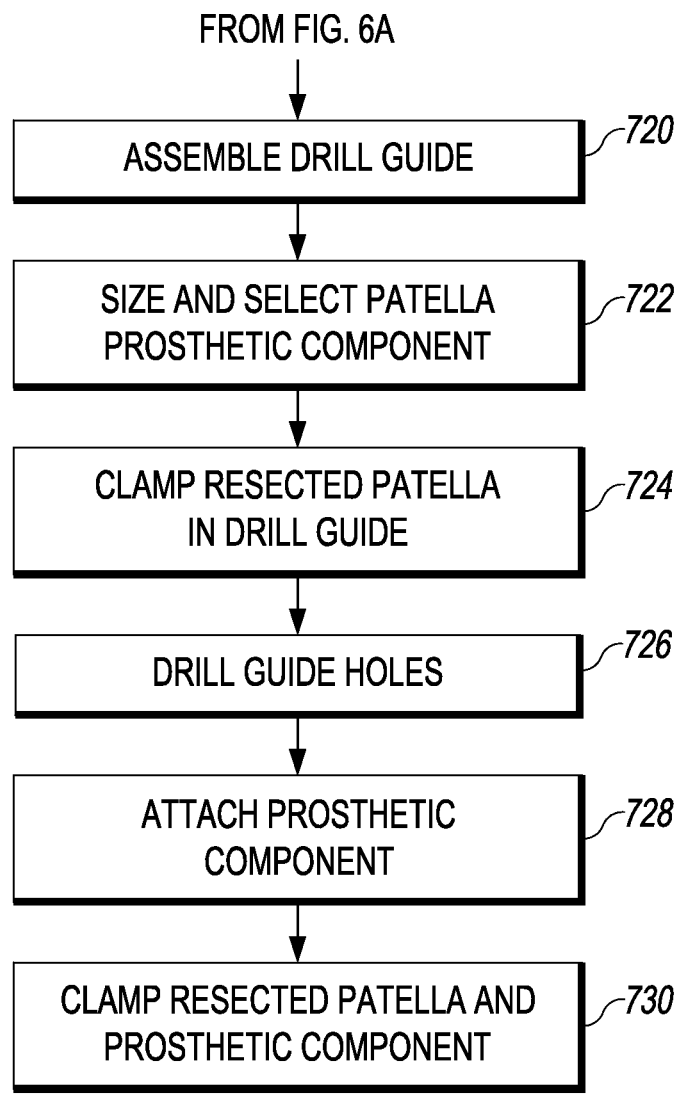
Figure 14:
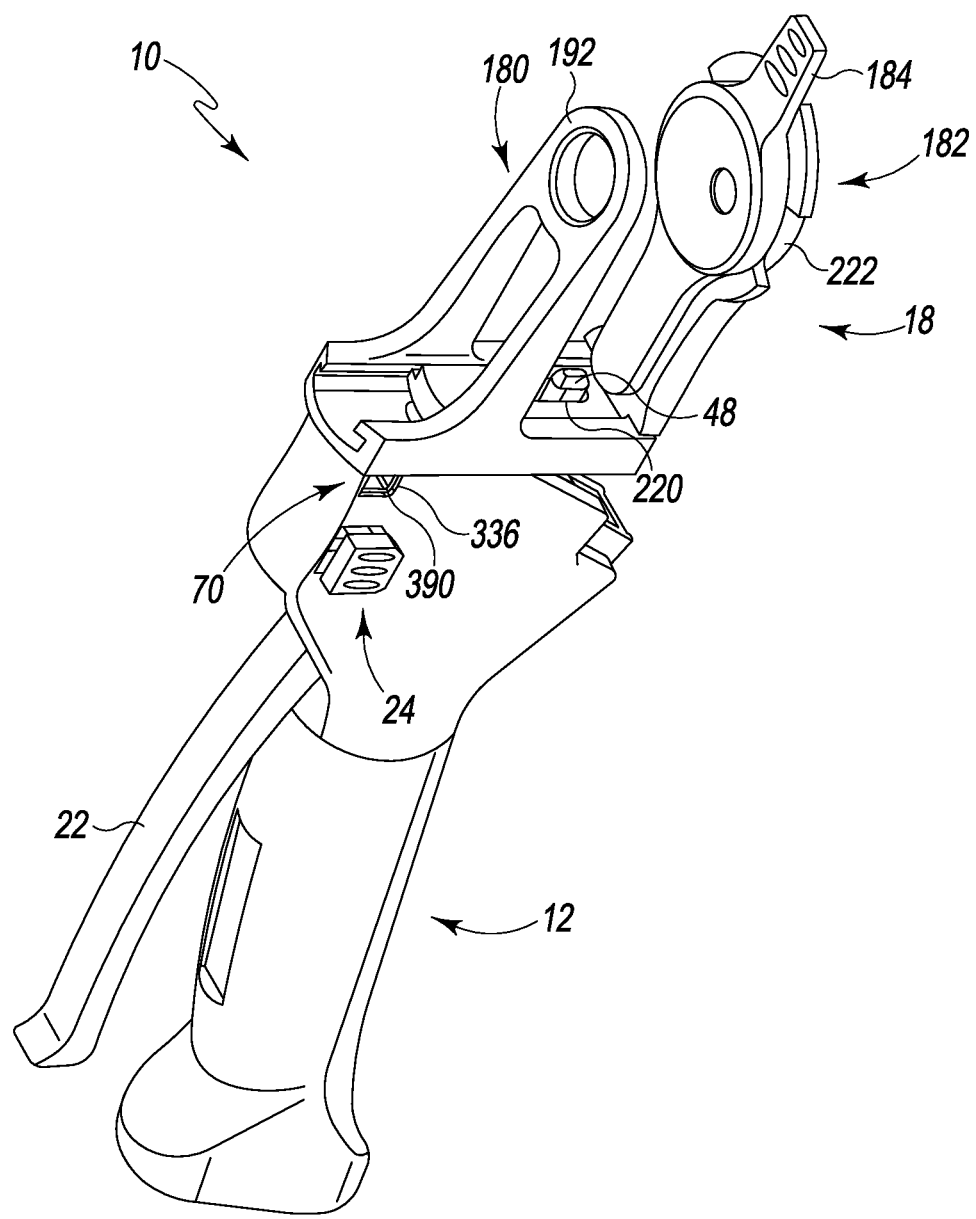
FIG. 14 is a perspective view of the orthopaedic surgical instrument assembly of FIG. 1 showing the patella drill guide attached the multifunctional handle.

Referring now to FIG. 6B, the surgical procedure 700 advances to block 720 in which the surgeon may attach the drill guide 18 to the multifunctional handle 12. To do so, the surgeon aligns the mounting bracket 70 of the drill guide 18 with the channel 336 defined in the mounting surface 32 of the handle 12. The surgeon also aligns the slot 220 defined in the drill guide 18 with the upper lever arm 48 of the handle 12. The drill guide 18 is then lowered onto the mounting surface 32 of the handle 12 such that the base 390 of the bracket 70 is received in the channel 336 and the upper lever arm 48 is received in the slot 220, as shown in FIG. 14. As described above, the locking mechanism 24 engages with the mounting bracket 70 to secure the drill guide 18 to the multifunctional handle 12.

In block 722 of the procedure 700, the surgeon may position the resected patella 676 between the support bracket 180 and the drill bracket 182 of the drill guide 18. To do so, the surgeon may rotate the gasket 184 of the drill guide 18 out of position between the brackets 180, 182. As shown in FIG. 15, the resected patella 676 may be positioned between the brackets 180, 182 such that an anterior surface 678 of the resected patella 676 faces the planar surface 532 of the backing plate 192 of the bracket 180 and a resected posterior surface 680 of the resected patella 676 faces the planar surface 552 of the drill plate 222 of the bracket 182.

The surgeon may use the drill guide 18 to size and select a patella prosthetic component 600. As shown in FIG. 15, the drill plate 222 has a rear face 682 that includes a plurality of indicators 684, each of which corresponds to one of a plurality of patella sizes. An outer circumference 686 of the body 550 indicates a patella size with a narrow cross-sectional area while the outer circumference 688 of the drill plate 222 indicates a patella size with a wide cross-sectional area. A plurality of etch marks 690 positioned between the circumferences 686, 688 indicate intermediate patella sizes. Using the indicators 684, the surgeon may select a patella prosthetic component 600 that offers the maximum coverage of the resected posterior surface 680 of the resected patella 676.

In block 724 of the procedure 700, the surgeon may clamp the resected patella 676 between the brackets 180, 182. To do so, the resected patella 676 is placed in contact with the backing plate 192 of the stationary arm 190 such that the teeth 542 of the backing plate 192 engage the anterior surface 678 of the resected patella 676. With the gasket 184 rotated out from the brackets 180, 182, the surgeon may operate the lever 22 of the multifunctional handle 12 to advance the drill plate 222 of the drill bracket 182 into contact with the resected posterior surface 680 of the resected patella 676. In particular, the surgeon squeezes the lever 22 to apply a predetermined amount of force to the trigger arm 50. The upper lever arm 48 acts on the inner wall 218 of the drill bracket 182 to advance the moveable arm 212 along the axis 140. As the moveable arm 212 of the drill bracket 182 moves, the drill plate 222 advances into contact with the posterior surface 680 of the resected patella 676, thereby engaging the teeth 562 of the drill plate 222 with the surface 680 and fixing the resected patella 676 between the brackets 180, 182 of the drill guide 18, as shown in FIG. 16.

In block 726 of the procedure 700, the posterior surface 680 of the resected patella 676 is surgically-prepared to receive the patella prosthetic component 610. As shown in FIG. 16, the surgeon may drill a series of pilot holes in the posterior surface 680 of the resected patella 676 that correspond to the position of the pegs 616 of the component 610. To do so, the surgeon may insert a surgical drill 692 into each of the guide holes 560 defined in the drill plate 222. The drill 692 passes through the guide hole 560 and contacts the posterior surface 680. The surgeon activates the drill and advances the drill 692 along the guide hole 560 until a pilot hole of sufficient depth is formed in the resected patella 676. The surgeon may then repeat the drilling operation at each of the guide holes 560 until the required pilot holes are created.

Returning to FIG. 6B, the procedure 700 continues to block 728 in which the surgeon may position the patella prosthetic component 610 on the surgically-prepared posterior surface 680 of the resected patella 676. The surgeon may apply cement to the anterior surface 614 of the component 610. After the component 610 is positioned over the resected patella 676, the pegs 616 may be advanced into the pilot holes formed in the surgically-prepared posterior surface 680 of the resected patella 676 until the anterior surface 614 is placed into contact with the posterior surface 680. The compression gasket 184 is then rotated back into position between the drill bracket 182 and the component 610. In that position, the plugs 592 of the compression gasket 184 are received in the guide holes 560 of the drill plate 222.

In block 730 of the procedure 700, the surgeon may clamp the component 610 to the resected patella 676, as shown in FIG. 17. To do so, the surgeon may squeeze the lever 22 to apply a predetermined amount of force to the trigger arm 50. The upper lever arm 48 acts on the inner wall 218 of the drill bracket 182 to advance the moveable arm 212 along the axis 140. As the moveable arm 212 of the drill bracket 182 is moved, the compression gasket 184 is advanced into contact with the posterior bearing surface 612 of the component 610. The component 610 is seated within and stabilized by the concave surface 600 of the gasket 184 such that the component 610 is clamped firmly to the resected patella 676 until polymerization is complete and the component 610 is secured to the resected patella 676.

Figure 18:
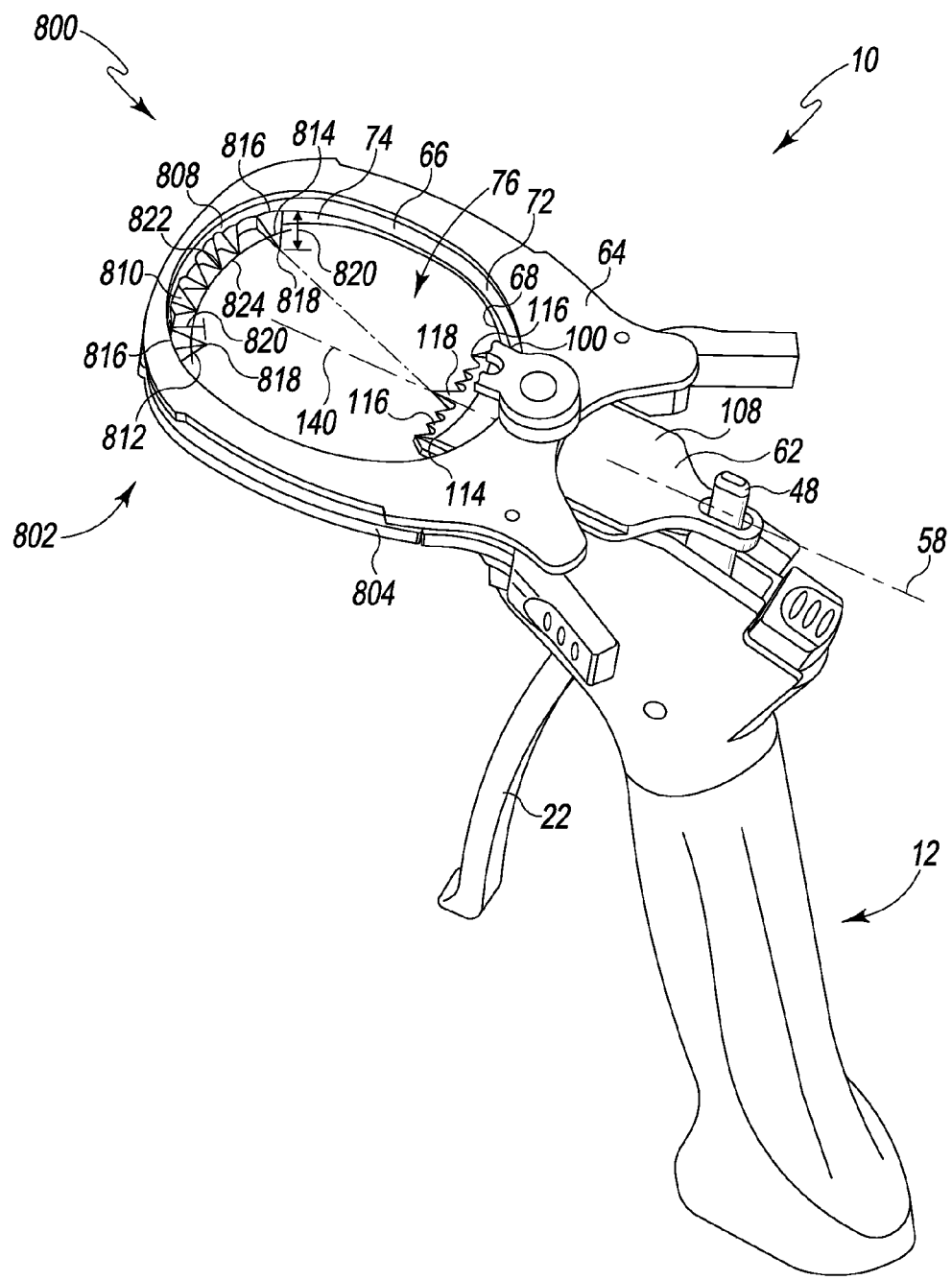
FIG. 18 is a perspective view of another embodiment of the patella resection guide of the orthopaedic surgical instrument assembly of FIG. 1.

It should be appreciated that in other embodiments, other patella resection guides can be used with the multifunctional handle 12. Referring now to FIG. 18, the orthopaedic surgical instrument assembly 10 is shown with a different embodiment of a patella resection guide (hereinafter referenced as a resection guide 800). Some features of the embodiment illustrated in FIG. 18 are substantially similar to those discussed above in reference to the embodiment of FIGS. 1-17. Such features are designated in FIG. 18 with the same reference numbers as those used in FIGS. 1-17.

The resection guide 800 includes a patella clamp 802 and a saw capture 64 configured to be removably coupled to the clamp 802. The clamp 802 includes a body 804 and a slide arm 62 moveably coupled to the body 804. Like the embodiment of FIGS. 1-17, the body 804 is formed from an implant grade metallic material such as steel, titanium, or cobalt chromium. It will be appreciated that in other embodiments the body 804 may be formed from a polymeric material such as polyethylene or UHMWPE. The body 804 has a substantially planar upper surface 66 and a lower surface 68 positioned opposite the upper surface 66. A mounting bracket 70, which is configured to be secured to the handle 12 via the locking mechanism 24, extends downwardly from the lower surface 68. When the clamp 802 is secured to the handle 12, the lower surface 68 of the clamp 802 is supported by the mounting surface 32.

As shown in FIG. 18, the upper surface 66 of the body 804 has an opening 72 defined therein. The body 804 includes a curvilinear inner wall 74 that extends downwardly from the upper surface 66 to the lower surface 68 and defines an oval-shaped aperture 76 through the body 804. Like the aperture 76 of the embodiment of FIGS. 1-17, the aperture 76 is sized to receive a patient's patella.

The body 804 of the patella clamp 802 also includes a jaw 808 extending from the inner wall 74. The jaw 808 has a plurality of teeth 810 that extend inwardly into the aperture 76. The teeth 810 include a pair of elongated teeth 812, 814. Each tooth 812, 814 has a base 816, a tip 818, and a length 820 from the base 816 to the tip 818 that is greater than any of the other teeth 810. The tips 822 of the remaining teeth 810 define an arc 824 within the aperture 76. The tips 818 of the teeth 812, 814 extend beyond the arc 824 into the aperture 76.

The body 804 of the clamp 802 further includes a track 100. As shown in FIG. 18, the slide arm 62 is positioned in the track 100 and is configured to slide along the track 100. The slide arm 62 has a main body 108, which includes a moveable jaw 114 formed opposite the jaw 808. The jaw 114 has a plurality of teeth 116 that extend toward the jaw 808. The teeth 116 include an elongated tooth 118 that has a length greater than any of the other teeth 116.

In use, when the patella resection guide 16 is coupled to the handle 12, the lever arm 48 is configured to act on the slide arm 62 to move the jaw 114 relative to the stationary jaw 808. As the upper lever arm 48 moves along the axis 58 relative to the housing 20, the slide arm 62 advances along the track 100, thereby moving the jaw 114 relative to the stationary jaw 78. As shown in FIG. 18, the slide arm 62 moves along an axis 140 that is defined by the tooth 118 of the moveable jaw 114.

As shown in FIG. 18, the teeth 812, 814 of the stationary jaw 808 are offset from the axis 140 defined by the tooth 118 of the moveable jaw 114. In the illustrative embodiment, the axis 140 is positioned between the teeth 812, 814, and the teeth 812, 814 are positioned equidistant from the axis 140. An axis 826 is defined between the tooth 118 and the tooth 812, and another axis 828 is defined between the tooth 119 and the tooth 814. Each of the axes 826, 828 extend at an angle relative to the axis 140.

In use, a patient's patella may be positioned in the aperture 76 of the resection guide 800. After adjusting the medial-lateral tilt as described above, the surgeon may lock the medial-lateral tilt of the patella by operating the lever 22 to move the jaw 114 to engage the patella with the elongated tooth 118 and one of the elongated teeth 812, 814. When the tooth 118 and the tip 818 of the tooth 812 or tooth 814 are sufficiently embedded in the patella, the surgeon may stop applying pressure to the lever 22. In that position, the remaining teeth 116, 810 of the jaws 114, 808 are spaced apart from the patella. With the tooth 118 and one of the elongated teeth 812, 814 embedded in the patella, rotation of the patella about an axis extending the inferior-superior direction is prevented and the medial-lateral tilt of the patella is locked. The surgeon may then set the superior-inferior tilt by rotating the patella about one of the axes 818, 820 before engaging the patella with remaining teeth 116, 810 of the resection guide 800.

Figure 19:
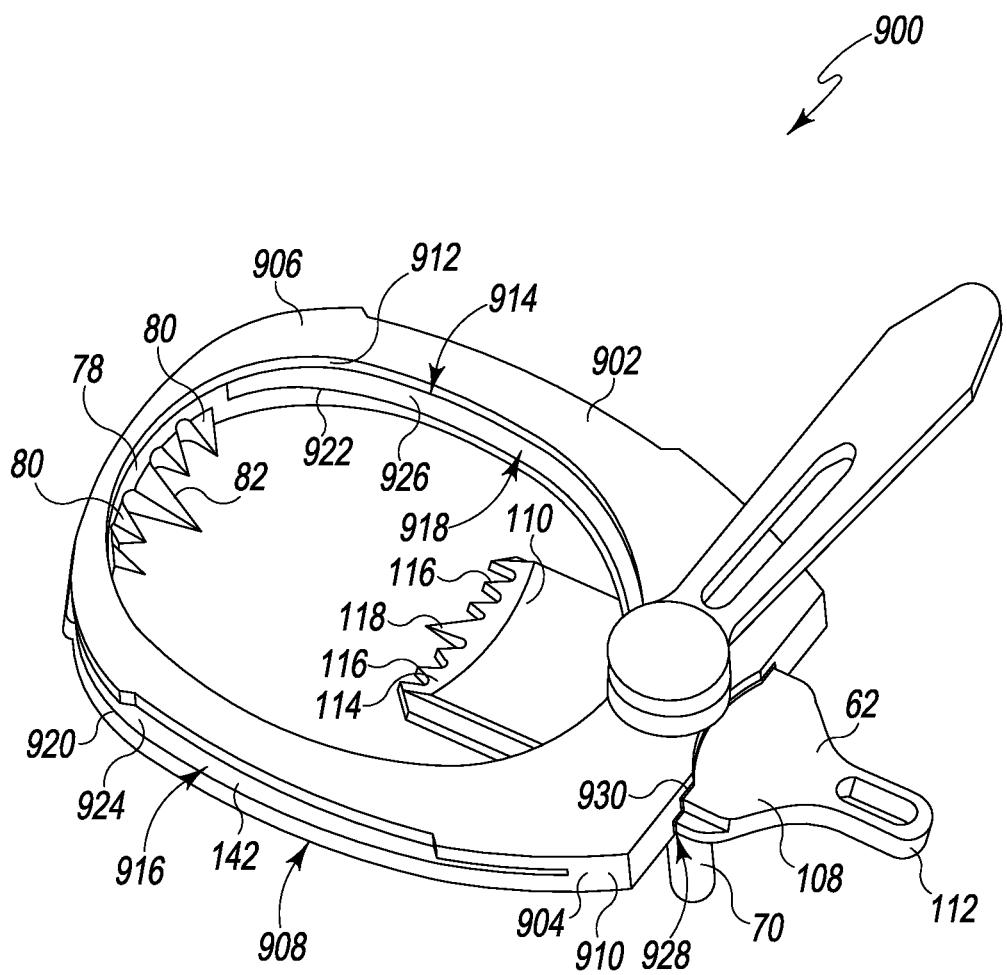
FIG. 19 is a perspective view of another embodiment of the patella resection guide of the orthopaedic surgical instrument assembly of FIG. 1.

Referring now to FIG. 19, another embodiment of a patella resection guide (hereinafter referenced as a resection guide 900) is shown. Some features of the embodiment illustrated in FIG. 19 are substantially similar to those discussed above in reference to the embodiment of FIGS. 1-17. Such features are designated in FIG. 19 with the same reference numbers as those used in FIGS. 1-17. The resection guide 900 including a frame 902 having a mounting bracket 70 extending downwardly therefrom. As discussed above, the mounting bracket 70 is configured to be secured to the handle 12 via the locking mechanism 24.

The frame 902 includes a body 904 and a clamping or slide arm 62 that is moveably coupled to the body 904. The frame 902 is formed from an implant grade metallic material such as steel, titanium, or cobalt chromium. It will be appreciated that in other embodiments the body 904 may be formed from a polymeric material such as polyethylene or ultra-high molecular weight polypropylene (UHMWPE).

The body 904 of the resection guide 900 has an upper surface 906, a bottom surface 908, and an outer wall 910 connecting the surfaces 906, 908. A curvilinear inner wall 912 extends downwardly from the upper surface 906. The curvilinear inner wall 912 defines a substantially elliptical or oval-shaped aperture 914 through the body 904. The aperture 914 is sized to receive a patient's patella, as will be described in greater detail below. It will be appreciated that in other embodiments the aperture 914 may have a different size or shape, such as, for example, a square, rectangle, or other shape properly sized to receive a patient's patella.

The body 904 also includes a pair of cutting guide slots 916, 918 on each side thereof. Each of the slots 916, 918 extends from an opening 920 defined in the outer wall 910 to an opening 922 defined in the inner wall 912. Planar surfaces 924, 926 extending between the openings 920, 922 define the bottom surfaces of the slots 916, 918, respectively. The surfaces 924, 926 further define a resection plane 142 that extends through the patella when the patella is positioned in the aperture 914.

The body 904 also includes a jaw 78 extending from the inner wall 912. The jaw 78 is embodied as a plurality of teeth 80 that extend inwardly into the aperture 914. The teeth 80 include an elongated tooth 82 having a length greater than any of the other teeth 80 like the elongated tooth 82 of the embodiment of FIGS. 1-17. Opposite the jaw 78, the body 904 has a track 928 defined therein. The track 928 extends between an opening (not shown) defined in the inner wall 908 and an opening 930 defined in the outer wall 910.

The slide arm 62 of the frame 902 is positioned in the track 928 and is configured to slide along the track 928. The slide arm 62 has a main body 108 including an end 110 positioned opposite the jaw 78 of the body 60 and another end 112 configured to engage the lever 22 of the multifunctional handle 12.

The slide arm 62 also includes a moveable jaw 114 formed at the end 110 opposite the jaw 78. The jaw 114 is embodied as a plurality of teeth 116 that extend toward the jaw 78. The teeth 116 include an elongated tooth 118. The elongated tooth 118, like the elongated tooth 118 of the embodiment of FIGS. 1-17, has a length that is greater than any of the other teeth 116.

In use, a patient's patella is positioned between the jaws 78, 114, and the teeth 80, 116 of the jaws 78, 114 are configured to engage the patient's patella to hold the patella in position during a resection procedure. The planar surfaces 924, 926 are usable by the orthopaedic surgeon to guide the surgical saw blade during the resection procedure and thereby define the resection plane 142 through the patella.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of surgically preparing a patella for implantation of a patella prosthetic component, comprising:
    positioning the patella between a pair of jaws of a patella resection guide,
    rotating the patella about a first axis extending in an inferior-superior direction to adjust the medial-lateral tilt of the patella,
    engaging the pair of jaws with the patella such that rotation about the first axis is prevented,
    rotating the patella about a second axis extending in a medial-lateral direction to adjust the inferior-superior tilt of the patella while the pair of jaws engage the patella,
    clamping the pair of jaws to the patella after rotating the patella about the second axis such that rotation about the first axis and the second axis is prevented, and
    engaging the patella with a cutting saw blade after clamping the pair of jaws.

2. The method of claim 1, wherein the pair of jaws includes a stationary first jaw and a second jaw that is moveable relative to the first jaw.

3. The method of claim 2, wherein engaging the pair of jaws further includes engaging a first tooth of the first jaw with the lateral side of the patella and advancing a second tooth of the second jaw into contact with the medial side of the patella.

4. The method of claim 3, wherein the first tooth and the second tooth define the second axis, and rotating the patella about the second axis includes rotating the patella on the first tooth and the second tooth.

5. The method of claim 2, wherein clamping the pair of jaws with the patella includes engaging additional teeth of the first jaw with the lateral side of the patella and engaging additional teeth of the second jaw with the medial side of the patella.

6. The method of claim 1, wherein positioning the patella between the pair of jaws includes contacting the patella with a height gauge of the patella resection guide.

7. The method of claim 1, further comprising securing a saw capture to a body of the patella resection guide, the body having the pair of jaws coupled thereto.

8. The method of claim 1, further comprising measuring the patella to determine a level of bone resection, wherein engaging the patella with the cutting saw blade includes cutting the patella to the level of bone resection.

9. A method of surgically preparing a patella for implantation of a patella prosthetic component, comprising:
    attaching a patella resection guide to a handle,
    operating a lever of the handle to engage a pair of jaws of the patella resection guide with a patient's patella,
    engaging the patella with a cutting saw blade to resect the patella and create a resected patella,
    detaching the patella resection guide from the handle,
    attaching a patella drill guide to the handle,
    operating the lever of the handle to clamp the resected patella between a pair of brackets of the patella drill guide by (i) contacting the anterior side of the resected patella with a first bracket, and (ii) advancing a second bracket into contact with the posterior side of the resected patella,
    drilling at least one mounting hole in the resected patella by advancing a surgical drill through one of a plurality of guide holes defined in the second bracket,
    operating the lever to withdraw the second bracket from the posterior side of the resected patella after drilling at least one mounting hole,
    attaching the patella prosthetic component on the posterior side of the resected patella, and
    operating the lever to clamp the patella prosthetic component and the resected patella between the pair of brackets.

10. The method of claim 9, wherein operating the lever of the handle to engage the pair of jaws includes contacting the lateral side of the patella with a first jaw, and applying an amount of force to the lever to advance a second jaw into contact with the medial side of the patella.

11. The method of claim 10, wherein operating the lever of the handle to engage the pair of jaws includes engaging a first tooth of the first jaw with the lateral side of the patella and engaging a second tooth of the second jaw with the medial side of the patella.

12. The method of claim 11, further comprising:
    rotating the patella about a first axis extending in an inferior-superior direction to adjust the medial-lateral tilt of the patella, and
    operating the lever of the handle to clamp the pair of jaws to the patella such that additional rotation about the first axis is prevented prior to engaging the patella with the cutting saw blade.

13. The method of claim 10, wherein detaching the patella resection guide includes operating the lever to withdraw the second jaw from the lateral side of the resected patella.

14. The method of claim 9, further comprising positioning a gasket between the patella prosthetic component and the second bracket prior to operating the lever to clamp the patella prosthetic component and the resected patella between the pair of brackets.

15. A method of surgically preparing a patella for implantation of a patella prosthetic component, comprising:
    positioning a resected patella between a first bracket and a second bracket of a patella drill guide,
    engaging the first bracket and the second bracket with the resected patella,
    advancing a surgical drill through one of a plurality of guide holes defined in the second bracket,
    drilling at least one mounting hole in the resected patella,
    disengaging the second bracket from the resected patella,
    attaching the patella prosthetic component to the resected patella,
    rotating a gasket coupled to the second bracket into position between the second bracket and the patella prosthetic component, and
    clamping the gasket, the patella prosthetic component, and the resected patella between the first bracket and the second bracket.

16. The method of claim 15, wherein engaging the first bracket and the second bracket with the resected patella includes engaging a first plurality of teeth formed on the first bracket with the anterior side of the resected patella and engaging a second plurality of teeth formed on the second bracket with the posterior side of the resected patella.

17. The method of claim 15, wherein rotating the gasket coupled to the second bracket includes placing a plug of a plurality of plugs extending from the gasket into each guide hole of the plurality of guide holes of the second bracket.

18. A method of surgically preparing a patella for implantation of a patella prosthetic component, comprising:
    positioning the patella between a pair of jaws of a patella resection guide including a first jaw and a second jaw that is moveable relative to the first jaw,
    adjusting the medial-lateral tilt of the patella by rotating the patella about a first axis extending in an inferior-superior direction,
    engaging a first tooth of the first jaw with a lateral side of the patella and engaging a second tooth of the second jaw with the medial side of the patella to prevent rotation of the patella about the first axis,
    adjusting the inferior-superior tilt of the patella by rotating the patella on the first tooth and the second tooth,
    clamping the pair of jaws to the patella such that movement of the patella is prevented, and
    engaging the patella with a cutting saw blade after clamping the pair of jaws.

* * * * *